(12) United States Patent
Homanfar et al.

(10) Patent No.: US 7,319,396 B2
(45) Date of Patent: Jan. 15, 2008

(54) RFID TRANSDUCER ALIGNMENT SYSTEM

(75) Inventors: Ramin Homanfar, Reno, NV (US); Bela Incze, Reno, NV (US); David Massey, Sparks, NV (US)

(73) Assignee: ABR, LLC, Reno, NV (US)

( * ) Notice: Subject to any disclaimer, the term of this patent is extended or adjusted under 35 U.S.C. 154(b) by 319 days.

(21) Appl. No.: 11/205,348

(22) Filed: Aug. 16, 2005

(65) Prior Publication Data

US 2006/0066453 A1    Mar. 30, 2006

Related U.S. Application Data

(60) Provisional application No. 60/602,751, filed on Aug. 18, 2004, provisional application No. 60/602,223, filed on Aug. 16, 2004.

(51) Int. Cl.
- G08B 13/14    (2006.01)
- A61B 6/14     (2006.01)
- G03B 42/02    (2006.01)
- G03C 5/16     (2006.01)

(52) U.S. Cl. ............... 340/572.1; 340/686.2; 378/170

(58) Field of Classification Search .......... 340/572.1, 340/686.2, 686.3, 686.4; 700/57; 702/150; 378/168, 170
See application file for complete search history.

(56) References Cited

U.S. PATENT DOCUMENTS

| | | | | |
|---|---|---|---|---|
| 3,548,209 | A | 12/1970 | Smith | 250/106 |
| 4,012,638 | A | 3/1977 | Altschuler et al. | 250/491 |
| 4,334,135 | A * | 6/1982 | Smith | 340/686.2 |
| 4,564,355 | A * | 1/1986 | Traiger et al. | 433/215 |
| 4,864,294 | A * | 9/1989 | Fukuhisa | 340/686.5 |
| 5,068,887 | A | 11/1991 | Hughes | 378/170 |
| 5,757,021 | A | 5/1998 | Dewaele | 250/581 |
| 5,828,722 | A | 10/1998 | Ploetz et al. | 378/38 |
| 6,047,257 | A | 4/2000 | Dewaele | 704/270 |
| 6,261,247 | B1 | 7/2001 | Ishikawa et al. | 600/587 |
| 6,359,628 | B1 | 3/2002 | Buytaert | 345/619 |
| 6,490,473 | B1 | 12/2002 | Katznelson et al. | 600/410 |
| 6,545,612 | B1 * | 4/2003 | Lindgren et al. | 340/686.6 |
| 6,762,429 | B2 | 7/2004 | Aonuma | 250/583 |

(Continued)

FOREIGN PATENT DOCUMENTS

CA    2016602    11/1991

(Continued)

Primary Examiner—John Tweel, Jr.
(74) Attorney, Agent, or Firm—Seed IP Law Group PLLC

(57) ABSTRACT

A radio frequency identification (RFID) system having the capacity to detect various geometric parameters of alignment. The described system is configured for use with dental x-ray, medical imaging and treatment, and customary and digital radiography apparatus, but is not restricted to such apparatus or applications. The system may include a multiplicity of RF transponders, RF tags, and RF readers, wherein each RF tag may include one or more carrier receive/data transmit coils and wherein each RF reader may include one or more carrier transmit/data receive coils, and wherein each coil of an RF tag or RF reader may resonate at one or more, and/or, at the same or differing frequencies. An RF tag located about an x-ray sensitive film or device, and an RF reader located about a dental x-ray machine or apparatus, are configured to be critically aligned, one to the other, rendering repeat imaging unnecessary.

45 Claims, 14 Drawing Sheets

U.S. PATENT DOCUMENTS

| | | | |
|---|---|---|---|
| 6,798,217 B2 * | 9/2004 | Scheible | 340/686.6 |
| 7,030,772 B1 * | 4/2006 | Lee et al. | 340/686.1 |
| 7,090,395 B2 * | 8/2006 | Glazer | 378/191 |
| 7,194,064 B2 * | 3/2007 | Razzano et al. | 378/168 |
| 7,216,054 B1 * | 5/2007 | Pchelnikov et al. | 702/150 |
| 2004/0008123 A1 | 1/2004 | Carrender et al. | 340/825.49 |

FOREIGN PATENT DOCUMENTS

| | | |
|---|---|---|
| EP | 1 374 791 | 1/2004 |
| JP | 60-210155 | 1/1987 |
| WO | WO 00/38570 | 7/2000 |

* cited by examiner

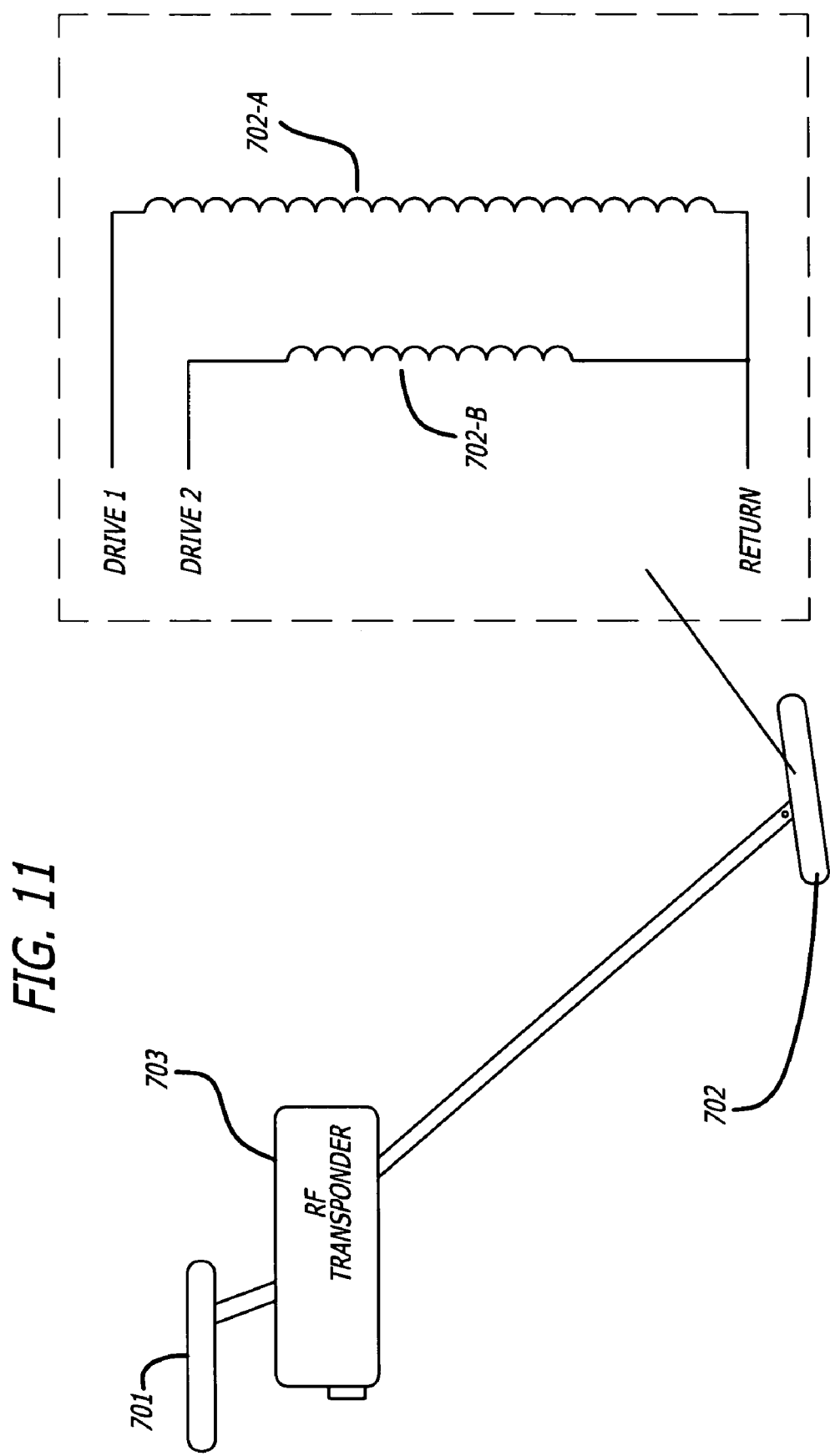

RFID TRANSDUCER ALIGNMENT SYSTEM

CROSS-REFERENCES TO RELATED APPLICATIONS

This application claims the benefit of U.S. Provisional Application Ser. No. 60/602,223, filed Aug. 16, 2004 and U.S. Provisional Application Ser. No. 60/602,751, filed Aug. 18, 2004, the contents of which are hereby incorporated herein by reference.

BACKGROUND OF THE INVENTION

This invention relates generally to providing enhanced functionality with regard to common radio frequency identification (RFID) technologies and devices, and more specifically, to the utilization of electromagnetic flux fields of at least one predetermined radio frequency (RF) to detect various geometric alignment conditions of two or more items, devices, or apparatus to each other in three dimensional space, for example, as an x-ray system positioning apparatus, the invention provides for detection and indication of the relative positionings, ergo: various geometric alignment conditions, as might exist between an x-ray emissions device, and, an RFID tag coupled with an x-ray sensitive film or apparatus.

In general, function of a given RFID tag is to act as a "remote sensor device" for a given RFID transponder (ie: an electronic apparatus which is coupled to an RF sense coil). When enabled, an RFID transponder's sense coil (also known as a carrier transmit/data receive coil, or reader), produces an electromagnetic field of flux at a predetermined frequency, which creates a radiated "carrier" transmit signal. When an RFID tag is placed in close proximity to an enabled RFID transponder's sense coil, the RFID tag eventually "powers up". The RFID tag, being impressed with the carrier transmit signal, becomes activated. This occurs by the fact that an LC tank circuit, generally comprised of a capacitor and a carrier receive/data-transmit coil, within the RFID tag begins to self-oscillate, which creates a secondary electromagnetic (EM) field of flux at a predetermined frequency within and about the RFID tag. Soon after the RFID tag is activated, the RFID tag begins to transmit a serial data stream of "canned/stored" information. Data transmission is generally accomplished by means of electronic components within the RFID tag shunting the LC tank circuit, according to the RFID tag's design criteria and predefined data protocol, etc.

When an RFID tag begins to oscillate so as to radiate a specific RF signal and electromagnetic field of flux, the RFID transponder sense coil becomes impressed with the RFID tag's "return" RF signal. The return RF signal impressed upon the RFID transponder sense coil is commonly referred to as "backscatter" or a backscatter signal. In concert with effects produced by "near-field inductor coupling", the backscatter signal generally alters certain characteristics of the RFID transponder carrier-transmit signal. Such carrier-transmit signal alterations, even as they might be minute initially, can be detected by appropriate RFID transponder "front-end" circuitry. When actual RFID tag serial data stream transmission occurs, the RFID transponder acts to detect the backscatter signal, generally, through the use of an "envelope detector" circuit. The RFID transponder will then condition/filter and amplify the backscatter signal to obtain a resultant "clean" data stream signal. Thereafter, the RFID transponder's microcontroller may "test/decode/read" and be configured to respond to the resultant signal, for example, by inputting a product name, code and price into a cash register when an item containing an RFID tag is scanned, or by setting off an alarm when someone walks out of a store without purchasing an item containing an RFID tag. However, current RFID technology has routinely been limited to its namesake: product "identification". Thus, the technology has not been applied in alternatively new ways, or with regard to differing applications. Accordingly, common RFID technology does not provide for geometric alignment functionalities, such as indicating best non-contact alignment between an x-ray emitter and an x-ray film during the positioning of one to the other.

During the traditionally standard process of taking dental x-rays, special tools and several tedious steps are often required. Two options for taking x-rays are well known wherein: 1) a molded x-ray film holder, which generally has sharp edges around its periphery, is loaded with an x-ray film and together is placed in a patient's mouth to bite down on (which is most discomforting for most patients due to the sharp edges), such that a dental technician or doctor must then visually estimate the position of the film holder so as to take an x-ray; or, 2) wherein a molded x-ray film holder, also having sharp edges around its periphery, is loaded with an x-ray film and together is placed onto a "RINN SYSTEM" apparatus (a long bar, generally of metal, with an x-ray film holder receiving device at one end, and an x-ray "head" apparatus receiving device at the other end), which is then collectively placed in a patient's mouth to bite down on (which is extremely discomforting for most patients due to the sharp edges, as well as due to the bulkiness of the RINN apparatus) with the metal bar and x-ray head apparatus receiving device protruding from the patient's mouth such that a dental technician or dentist would then place the x-ray head into the x-ray receiving device so as to take an x-ray radiograph.

Aside of the general need for special alignment tools, the disadvantages of the above two options are several: 1) often additional x-rays are required to be taken because of improper alignment of the x-ray head apparatus to the x-ray film, especially when the location/position of the x-ray film is manually estimated, and often, when; 2) the RINN SYSTEM is improperly located/positioned in a given patient's mouth, which creates; 3) loss of both time and supplies, increasing expense, and, which additionally; 4) exacerbates a given patient's discomfort. The present invention was devised to overcome these challenges with graceful simplicity. The first concept considered was to provide a system that might permanently eliminate the need for a RINN SYSTEM device/alignment tool. The second concept considered was, in part, to alter the design of the common x-ray film holder device so as to eliminate its sharp edges, and provide means to accurately locate/detect it's position, as attached with an x-ray film, once hidden inside a patient's mouth. The third concept was to identify a system by which the taking of dental x-rays would become less intrusive, yet more accurate.

RFID technology appears to offer the most ideal solution to the current challenges associated with obtaining dental x-rays, yet-RFID technology, in practice and application, has customarily been used for product and other commodity "identification" purposes. Such technology had not been used for exacting a critical alignment of an x-ray head apparatus to an (often hidden) x-ray film. One aspect unknown in the prior art was a system that would permit placement or attachment of a predetermined RFID tag (aka: RF tag) on or about a common x-ray film or x-ray film holder device. Such a system would also provide for RF tag placement or attachment to or about newer technology (ie: digital radiograph sensors). In this, an enhanced RF tag architecture and device is required, as are various methodologies with which to embed or place the new RF tag.

Another aspect unknown in the prior art is an electronics design that would act as a dental RFID transponder (aka: RF transponder), and that could have a remote yet attached sense coil. Such a coil, which acts to enable the new RF tag device and also acts to receive data from an enabled new RF tag device, would need to be devised so as to fit upon/mechanically interface to the active end of a given dental x-ray head apparatus.

One issue in creating a dental-oriented non-contact RFID transducer system is that a given dental RF tag ought be physically smaller than an accompanying dental RF carrier transmit/data receive coil. Another issue to operational practicality for a dental application is that "non-contact" operation be obtained, wherein a given x-ray head apparatus would never (intentionally, nor need to be caused to) touch a patient's face, in the course of alignment of the x-ray head apparatus to the dental RF tag within a patient's mouth. This issue is not in the least trivial since known RFID technology did not allow for spacious RF tag distance sensing in wholly scaled-down RFID systems. Various common RF tags currently available were used in test beds, and were found to be grossly lacking as it concerned desired functionality and operational distance to a similarly available RF transponder.

It was found that when an RF tag was placed in a patient's mouth and behind the teeth (as would normally occur in a dentist's office), valid sensing-distance was no more than one inch, and often much less. An RF transponders carrier transmit/data receive coil needed to be placed inward on, at, or extremely close to the cheek in order to "read" a common RF tag. Thus, commonly available systems were both nonideal and impractical for a dental x-ray application. Therefore, there is an additional need for an enhanced RF transponder circuit design having additional features, and an enhanced carrier transmit/data receive coil circuit design.

As will be appreciated by those of skill in the art, providing.a dental x-ray RFID positioning and alignment system incurs several design challenges, including: 1) dental RF tag size, which being rather small, produces only a small RF field of flux at resonance; 2) sensing distance to a given RF tag of at least two inches is desirable; 3) dental RF transponder carrier transmit/data receive coil size, which also being rather small, has a limited range for detecting a radiated RF signal from a remoted RF tag when an RF tag is activated; 4) data stream signals received by a dental RF transponder carrier transmit/data receive coil are often in the microvolt range when the RF tag is several inches away; 5) such signals, when then fed into operational amplifier circuits, generally can not be distinguished or easily separated from base-noise levels of operational amplifier circuits, and thus, 6) the resultant signals from the operational amplifier circuits contain inherent and free-air radiated noise, as well as the desired data signals, and also include RF carrier transmission components, making "valid" signal detection difficult; and 7) even with filtering, free-air radiated alternating current (A.C.) signals are amplified and become part of the net/final signal structure from the operational amplifier circuits, thereby, grossly affecting final signal integrity, particularly when obtained by a highly sensitive RF transponder analog front-end circuit.

Thus, what is needed and heretofore unknown is an RFID transducer non-contact alignment system that fulfills dental and other x-ray application requirements, that solves the above identified technical challenges, and that provides cost effective simplicity of operation. There is also a need for RFID-type technology operable over greater distances between certain types of RF tags and RF transponders. There is also a need to fill the technological gaps and voids in the practical applications of RFID technology. There is a further need for an ability to offer RFID alignment functionality to establish and provide for new applications within the RFID industry, especially with regard to the critical alignment of two or more items, devices, or apparatus to each other in three dimensional space.

SUMMARY OF THE INVENTION

The present invention is directed to a new application for RFID technology that is intended to enhance the industry as a whole. The RFID system of the present invention utilizes certain design methodologies so as to provide inexpensive and uncomplicated apparatus for detecting and indicating various RFID tag-to-RFID transponder sense coil alignments.

The present invention provides a simple, functionally enhanced, and new RFID system concept, wherein presently available RFID systems have opportunity to be improved upon or expanded by various new features and/or functionalities, including the capacity to detect manifold parameters of alignment. The present invention further provides a new type of RFID system specifically designed for the dental industry, medical imaging systems, and other such industries, including use with digital radiography. The present invention and new technology also provides a new RFID system having new types of RF transponders, RF readers, RF tag devices, and x-ray film holders. The new technology allows presently utilized dental x-ray films to be placed into a re-devised, intelligent and more comfortable (for the patient) film holder. The present invention and new technology also provides for embedding an RF tag device directly with an x-ray sensitive film, and additionally may be applied to contemporary x-ray systems or digital x-ray systems, allowing contemporary x-ray films or digital x-ray imaging sensors to be critically aligned to a given dental x-ray machine head apparatus, rendering repeat imaging unnecessary.

The present invention also provides a new RFID system, wherein dental x-rays may be taken with great accuracy resulting from the ability to denote critical alignment of an x-ray emissions apparatus to a dental x-ray film or digital x-ray imaging sensor in a patient's mouth, and in a noncontact manner. The system of the present invention may be configured to denote critical alignment of a dental x-ray film or digital x-ray imaging sensor within a patient's mouth without the need for commonly used special tools, procedures or devices. The new RFID system may be configured to store patient and other information in the RF tag device and/or x-ray film holder.

The present invention includes a new RFID system for use with x-ray and/or other radiography imaging apparatus so as to provide an automatic RF tag seek mode of operation. For example, a given x-ray head apparatus may be configured to move on its own accord when prompted by the RFLD system. When enabled, the x-ray head apparatus may locate a (perhaps) hidden RF tag device, such as during a dental application, and ultimately align itself to a given located RF tag device. The x-ray head apparatus may be further configured to automatically obtain a.desired x-ray image, and/or retrieve or store certain data from/to an RF tag. The x-ray head apparatus may be further configured so that the apparatus cannot activate and provide a radiograph unless/until a predetermined alignment to a given RF tag device has occurred. Such a system provides a new safety mechanism against impromptu enabling of an x-ray machine apparatus and thus reduces x-ray exposure for the patient.

The present invention improves upon the present designs of certain RFID transponder devices, by providing for one or a multiplicity of RF transponder carrier transmitdata receive coils, depending on application and/or need. One or a multiplicity of RF transponder carrier transmit/data receive coils or RF readers may be provided in a given system, depending on the application and/or need, each resonant to the same, or differing frequencies. In a multiple coil system, and depending on the application, the size of the RF transponder carrier transmit/data receive coils may vary. Further, the multiplicity of RF transponder carrier transmit/data receive coils may be fixed about a given RF transponder enclosure, and/or, placed remote from the from the RF transponder by using one or more appropriate cable devices.

The present invention provides for improving upon the present designs of certain RFID transponder devices, allowing for use with hand-held, fixed-in-place, stationary and permanently mounted applications. Such hand-held, fixed-in-place and similar applications may be operated from various applied power sources, for example, by means of alternating current (A.C.) supplied by a wall socket, and/or direct current (D.C.) supplied by a battery.

The present invention improves upon the present designs of certain RFID transponder devices by providing a system for indication of the detection and presence of a given RF tag by a given RF transponder by various devices and circuits, including either or both: audio or visual techniques and/or apparatus. The system provides for indication, within pre-defined limits, of the distance from a given RF transponder's carrier transmit/data receive coil to a given detected RF tag by various devices and circuits, including either or both audio or visual techniques and/or apparatus. The system also provides for indication of the detection of valid data from a given detected RF tag by a given RF transponder by various devices and circuits, including either or both audio or visual techniques and/or apparatus.

The present invention improves upon the present designs of certain RFID transponder devices by providing a system for indication of various alignment conditions, including at least one critical alignment condition of a given detected RF tag by a given RF transponder by various devices and circuits, including either or both audio or visual techniques and/or apparatus. The system may provide indication of a given RF transponder's status, such as "elapsed warm-up time", and/or "ready for operation", for example, from various devices and circuits such as from audio or visual techniques and apparatus. The system may also provide for indication of a given RF transponder's carrier transmit frequency or frequencies from such devices, circuits and techniques. The system may also provide for varying, and indication of the variance, of a given RF transponder's carrier transmit frequency or frequencies. Further, the system provides for tuning/detuning and indication of a given RF transponder's carrier transmit frequency or frequencies by various devices and circuits, including either or both audio or visual techniques and/or apparatus.

The present invention improves upon the current designs of certain RFID transponder devices by providing a system for selection and indication of a given RF transponder's explicit carrier transmit drive signal waveform or waveforms by various devices and circuits, including either or both audio and visual techniques and/or apparatus. The system may also provide for indication of a given RF transponder's carrier transmit amplitude or amplitudes by such devices, circuits and techniques. The system may further provide for indication of the presence of a given RF transponder's carrier transmit signal or signals from such devices, circuits and techniques. The system also may provide for indication of the presence of a given RF transponder's carrier transmit/data receive coil or coils. Further, the system may provide for selection, as well as the indication of selection, of one or more carrier transmit/data receive coils attached to a given RF transponder. Also, the system may provide for the indication of the current mode of operation of a given RF transponder (such as idle or seek mode) by various devices and circuits, including either or both audio or visual techniques and/or apparatus.

The present invention improves upon the current designs of certain RFID transponder devices by providing a system for on-the-fly and/or in-situ RF tag programming and the indication of the same by various devices and circuits, including either or both audio or visual techniques and/or apparatus. The system may provide for sensing various parameters of alignment, including the parameter of critical alignment, in a fixed or variable three-dimensional space and indication of the same by such devices, circuits and techniques. The system may further provide for audio instruction and/or feedback for a user in the course of operation, whether in the form of tones and/or voice by various devices and circuits. Further, the system may provide for audio instruction and/or feedback for a user in the course of operation, whether in the form of tones and/or voice, wherein pitch and/or volume, or expression, or such, by said various devices and circuits, that might be selected and/or managed by a given RF transponder's response to certain sensed system signals or conditions, alignment parameters, user input, or other predefined variables.

The present invention improves upon the current designs of certain RFID transponder devices by providing a system having a user keyboard of some nature, whereby a user may, for example, input or set or define certain data or criteria, or retrieve information and other data from, or apply certain information or data to, various devices and circuits. The system may also be configured with one or more display apparatus, primarily for user feedback, whether it or they be LED or LCD, or the like, in nature or a mixture thereof. The system may provide for at least one external communications port. Such an external communications port may accommodate a transmission/data link to/with a computer and/or a printer. Further, the system may provide for remote placement of certain visual indicators and/or audio devices near or at a given RF transponder carrier transmit/data receive coil and/or upon an RF transponder.

The present invention improves upon the present designs and functionality of RFID transponder devices and systems and their components by providing not only for RF tag or sensor device detection and reading and/or sorting, and/or other functions as pertinent to a given application, but for programming various digital-formatted data into a given RF tag or sensor device, by various devices and circuits, and further provides for detection of the position of an RF tag to an RF sense coil, by various devices and circuits.

The present invention includes a method for constructing an RF tag envelope from a rubber, plastic, vinyl, or other suitable material, so as to allow for dental x-ray film insertion or digital x-ray imaging sensor attachment. The RF tag envelope, containing an electronics circuit, may also be constructed from such materials so as to allow for dental x-ray film insertion or digital x-ray imaging sensor attachment. Such an RF tag envelope may be fabricated so as to allow for dental x-ray film insertion or digital x-ray imaging sensor attachment, wherein the electronic circuit may be minimally comprised of a coil apparatus, a capacitor device, a power conditioning circuit and a microcontroller circuit device.

The present invention further includes a method for constructing and fabricating an RF transponder envelope from plastic, metal, or other suitable material. The RF transponder envelope may include a printed circuit board apparatus and whereon various and sundry electronic components may be attached. The electronic components on the circuit board may include certain discrete analog and digital electronic devices, passive electronic devices, a microcontroller circuit device, various switches, and visual display and/or audio devices. The circuit board may also include or have attached one or more connectors, including that of an applied power source connector.

The present invention also includes a method for constructing and fabricating an RF reader envelope from plastic, vinyl, or other suitable material for use with a dental x-ray machine head apparatus attachment, such as insertion. The RF reader envelope may be fabricated, so that a dental x-ray machine head apparatus is attached or inserted on one end, and a coil apparatus may be constructed about the opposite end of the envelope. Such an RF reader envelope may be configured so that visual or audio indicator devices and one or more connector devices may be attached to the envelope. Such connector devices may attach to one or more cable apparatus so that the RF reader envelope may ultimately be attached to an RF transponder envelope.

The present invention includes a method for constructing and fabricating an RF tag envelope from paper, rubber, plastic, vinyl or other suitable material. The RF tag envelope may be configured with various and sundry electronic components and that the electronic components form a circuit minimally comprised of a coil apparatus, a capacitor device, a power conditioning circuit and a microcontroller circuit device so as to construct an RF tag device. Such an RF tag device may be configured for attachment about a digital radiography apparatus or in synchronicity with customary x-ray imaging apparatus, for example, x-ray film requiring an x-ray film holder.

The present invention further includes a method for utilizing an RF tag device, RF reader device, and an RF transponder device, each in a completely assembled form, wherein each component is configured to work in synchronicity with each of the other components. The components may be further configured together and collectively to form and operate as an RFID transducer alignment apparatus and system. Such an RFID transducer alignment apparatus and system may function and be used as a non-contact alignment apparatus and/or tool. In certain applications the RFID transducer alignment apparatus and system may be configured to perform more basically as a common yet enhanced RFID system.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 11 is a schematic representation of an alternate embodiment of an RF transducer alignment system of the present invention illustrating a multi-form RF reader.

DETAILED DESCRIPTION OF THE PREFERRED EMBODIMENTS

Figure 1:
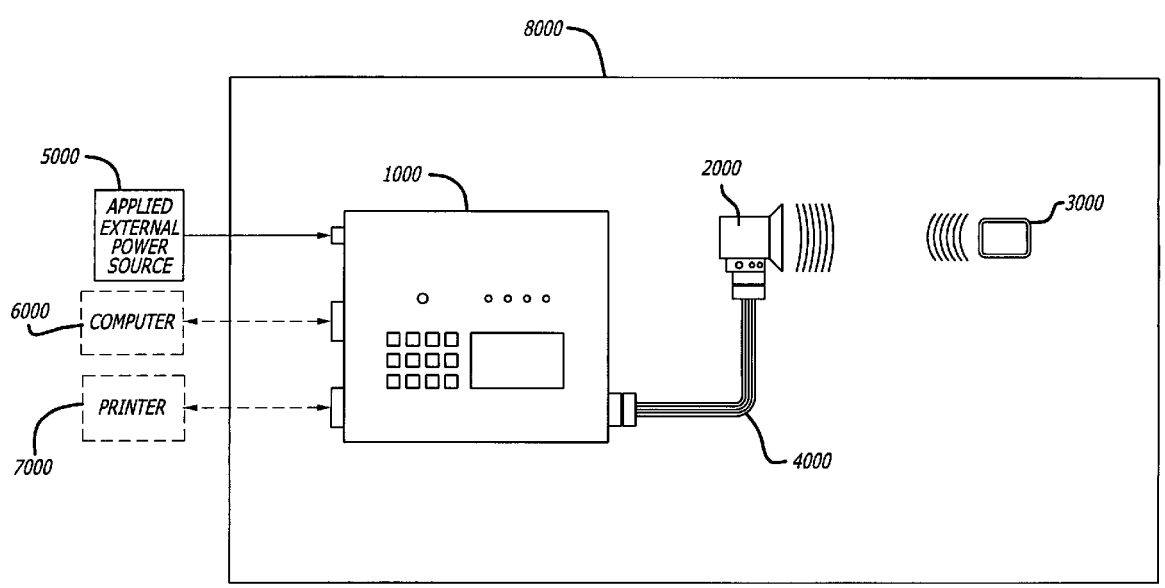
FIG. 1 depicts a system diagram of an embodiment of an RFID transducer alignment system generally devised for dental applications according to the present invention.

As shown in the drawings for purposes of illustration, the present invention is directed to a beneficial and novel electronic design, the basis of which is founded on RFID (radio frequency identification) technology. The present invention provides an altogether new RFID application having enhanced levels of utility and practical functionality over present-day common\standard uses for/of the RFID technology. This RFID system is beneficially applicable to those apparatus or products that require, or might make use of non-contact power control and/or operation, non-contact accessibility or enabling, and non-contact entry. The invention is also useful for those products, apparatus, or devices that require or might make use of non-contact object/target sensing or detection, intelligent non-contact sensor response systems, and non-contact object/target data programming and/or data retrieval. The invention may also be applied to systems requiring non-contact alignment capability for example, dental/medical x-ray/imaging technologies. In addition, the invention is relevant to non-contact detection, monitoring, control and/or feedback for the specific alignment of certain systems and components of systems that would be enhanced by a remote alignment or positioning capability.

The system of the present invention is particularly applicable in the activity of proper positioning of a given x-ray machine head apparatus to a given x-ray film apparatus. The system utilizes a simple non-contact alignment procedure, without the need for implementing "customary" alignment devices or techniques. The system is applicable to newer technology (for example, digital radiography) and to established technologies, such as x-ray film and x-ray holder devices. As a function of operation, the present invention has the capacity to be utilized in many applications, wherein, and broadly speaking, an "RF tag" device (generally composed of a carrier-receive/data-transmit coil, a resonance capacitor, a power conditioning circuit, a microcontroller, and a coil shunting circuit) acts as a "remote target/sensor" or "system activation key." The RF tag is configured to interface to/with an "RF transponder" device, minimally composed of a carrier-transmit/data-receive coil (aka: sense, or reader coil), a resonance capacitor, a carrier transmit drive circuit, an applied data-receive signal detection circuit, various applied data-receive signal filters, various applied data-receive signal amplifier circuits, and various logic devices and/or a microcontroller wherein the RF tag and RF transponder, together, create a non-contact RF transducer alignment function and system. The system is configured such that when the RF transponder is in the near presence of the RF tag, then the RF transponder ultimately causes to occur one or more predefined actions or activities. Such actions may be determined by the real-world function(s) desired, application, and/or the type of end-user product manufactured.

The present invention provides for a non-contact RF transducer system minimally composed of at least one RF tag device and a control electronics package, such as an RF transponder. Together, the RF tag and RF transponder act to minimally perform as other RFID systems, yet may also provide for an RF transducer non-contact "alignment" system. The RFID system of the present invention may be adapted for use as an intelligent "item or device detector," an electronic non-contact pass-key system, a medical history bracelet/reader system, a computer enable apparatus, and a keyless car door and/or trunk opening system, as examples. As may be appreciated by those of ordinary skill in the art, many other applications for non-contact RFID sensor alignment exist that may benefit from a system configured to detect, monitor, and/or respond to the particular alignment of one apparatus to another. Such applications include when space docking one vehicle or platform to another, locating the internal communications port on a marine environmental transducer so data can be recovered from the transducer without opening its enclosure or using an external connector, and for use in exactingly monitoring the positioning of various hatches or flight-control surfaces, etc. on commercial aircraft. Numerous hand-held applications are apparent, for example, exactingly identifying the position of in-wall, underground/buried cabling or gas pipes, and the like, wherein homeowners and/or utility personnel could easily denote not only the "where" and/or "what" of what lies hidden from view, but perhaps, when installed or how deep, by using one or more concealed RF tag devices. Another hand-held application includes a luggage identification system, wherein ticket handlers may cause the programming and attachment of an RF tag to luggage. The benefit of such a system includes far more accurate and simple destination processing, and may also include insuring the rightful owner during baggage "pickup" should a question arise.

One benefit of the present invention is demonstrated when an RF tag is placed behind a given non-transparent material, and so not normally visible to a user/operator of the present invention, the user/operator may utilize the RF transponder to locate the RF tag (or vice versa). The RFID system may be used to locate the hidden RF tag and to also easily identify a "best-alignment" (of the RF tag to the RF transponder) scenario as well, if the latter is desired. In essence then, the RF transponder is, or may be, intended to identify the best position of/to, or "line-of-sight," of the RF tag to the RF transponder for then performing certain predefined activities. In some instances, the RF tag may or may not actually be hidden from view of the user/operator, however if alignment of an RF tag to an RF transponder is required, and if the alignment procedure is left solely to a human, wherein one might use a best guess or estimation process, and if the alignment is considered critical, positioning errors can occur in the attempt for alignment, providing the processes generally insure a "best-alignment" scenario fails to occur. The potential disadvantages of humanly performed alignment activities are overcome by the present invention, in that the present invention and RF transponder component thereof, inherently and automatically identifies a "best-alignment" scenario for a user/operator. In other applications, exacting alignment between the RF tag and RF transponder may at times not be critical, and that simple RF tag detection is all that is required. In other applications, perhaps utilizing a hand-held RF transponder unit, retrieving certain data a perhaps hidden RF tag may be keenly desired when the hand-held RF transponder is within "reading" distance of a given RF tag. In many such instances, less than perfect alignment between a given RF tag and an RF transponder is wholly acceptable and practical, as the present invention can easily allow for non-critical RF tag alignment detection and readings. Another example of an application of the system of the present invention includes locating and identifying hidden control knobs or valves and/or buried coupling devices. Such an application requires exacting location of such devices in order that one may accurately unveil the devices physical view before servicing or repairing or upgrading may be accomplished.

The present invention and its two main components (an RF tag device, and an RF transponder device) provide for one or more embodiments of the RF tag device. The RF tag remains minimally composed of 1) an LC tank circuit, having at least one carrier receive/data transmit coil of a predetermined value; 2) a resonant capacitor of a predetermined value to work in parallel with the carrier receive/data transmit coil, wherein both collectively act in response to a predefined applied carrier transmit signal, so as to be caused to resonate to/with the applied carrier transmit signal; 3) a power conditioning circuit, wherein a portion of the resonant energy generated by the LC tank circuit is used to create the required operating power for; 4) an on-board microcontroller device, wherein the microcontroller device can be configured to identify certain of the RF tag's operational parameters, and whereby a predetermined serial data stream may be generated from a predetermined protocol by using; 5) a carrier receive/data transmit coil shunting circuit; or 6) an LC tank circuit shunting circuit. As may be appreciated by those skilled in the art, present technology provides that an RF tag device does not require a battery power source for operation, but instead remains responsive to a near or close proximity externally applied carrier transmit signal and of a frequency that is conducive to cause resonance of a given RF tag's LC tank circuit.

The RF transponder may be a wall powered and/or battery operated device. The present invention provides for one or more embodiments of the RF transponder device, wherein the RF transponder remains minimally composed of 1) an LC circuit, composed of at least one carrier transmit/data receive coil of a predetermined value; and 2) a resonant capacitor of a predetermined value to work in series with the carrier transmit/data receive coil, wherein both collectively act in resonance to create a predefined applied carrier transmit signal; when 3) a predetermined carrier transmit drive signal is applied thereto; 4) an RF tag signal-detection circuit, the obtained signal of which is applied to; 5) predetermined filters and amplifier circuits, the resultant signal of which is then applied to; 6) a microcontroller device configured or programmed for desired operations and functions, as well as the ability to read the serial data transmitted by a given RF tag, whereby; 7) the microcontroller may cause to occur certain predetermined real-world activities, predicated on its associated predetermined firmware and input/output (I/O) circuitry and specific application or need.

Another aspect of the system of the present invention is to provide for remote placement of the transponder carrier transmit/data receive coil from the RF transponder electronics package, thereby providing a third main component of the system. Such a feature accommodates more easily the placement of an RF transponder coil (herein referred to as RF reader and/or RF reader device) in a given work area. This aspect may be accomplished through the attachment of a pre-configured cable between the RF transponder electronics package and its associated carrier transmit/data receive coil/RF reader. The system also provides for detecting and displaying the distance, within certain predefined limits, of the RF tag to an RF transponder carrier transmit/data receive coil. The system further provides the user with a visual indication of when the RF transponder detects the RF tag. Such detection can also act to wake a "sleeping" RF transponder microcontroller, or wake an RF transponder microcontroller that resides in "idle" mode. This feature also provides feedback to the user/operator that an RF tag detection has occurred. The visual indication is perhaps best accomplished with an LED (light emitting diode), particularly in terms of indicator life longevity and vibration resistance. The system may also provide the user with a separate visual indication of when the RF transponder detects a "readable/valid" data stream from a given RF tag. Predicated on data protocol and other data-form factors, such detection can act to cause an RF transponder microcontroller to ascertain the RF tag data stream to be valid and, thus, reliably useable. This feature also provides feedback to the user/operator that a given RF tag "reading" by the RF transponder may be in process.

It is also a function of the present invention to provide for those instances wherein one or more audio tones are desirable or required. An audio tone generator may provide additional feedback to the user/operator that tag detection or reading has occurred, for example, without need for the user/operator to look away from where or what he or she is presently (visually) focused on. The audio tone generator may simply provide for singular tone structures, or may provide pitch/frequency or volume changes (predicated, for example, on RF tag distance) and may offer voice feedback and/or commands. The system may also provide for RF tag detection with valid RF tag data-stream visual indicators and for an audio speaker device at or in close proximity to the RF transponder carrier transmit/data receive coil.

The system of the present invention may further be configured with a display device, such as a liquid crystal or OLED display. Such a display device may act to provide a user/operator with such predefined details as instructions, captured RF tag information, and other operational information. The system may be further configured to allow an RF transponder to interface with a computer and/or printer so as to remotely capture, display, and/or record some or all the information in a given RF tag.

The system of the present invention may be configured to provide for variable RF carrier transmit signal frequency control so as to utilize various RF tags by various manufacturers, having varying frequencies of resonance. Variation of the RF carrier transmit signal frequency can be implemented with such means as an adjustment potentiometer, or by a keyboard entry. Other mechanisms may be used, such as the switching in/out of various resonance capacitors; by altering the divide-by rate to/of certain logic devices; by a tunable coil device; or a combination thereof.

In addition, the system of the present invention may be configured to visually/audibly indicate when power has been applied to the RF transponder. Similarly, the system may visually/audibly indicate when a predefined warm-up period has elapsed and system stability has occurred. Such a feature is perhaps most desirable when a given electronics circuit utilizes a clock or oscillator circuit.

The system of the present invention may also visually/audibly indicate maximum (or even perhaps, less than maximum) carrier transmit signal strength/amplitude. The system may further allow for displaying a carrier transmit signal frequency, whether based upon an LED array and/or by using an alphanumeric or graphics display of some nature. In addition, the system may be configured with various mechanisms to provide for indication of the presence of a carrier transmit signal, and to provide for indication of the presence of a carrier transmit/data receive coil.

Further, the system of the present invention may provide selectable carrier transmit drive signal waveform control. The carrier transmit drive signal control may allow for the use of sine triangular or square waves, pulse width modulation or other signal waveform structures. The system may be configured to provide for carrier transmit drive signal frequency tuning/detuning control circuitry. Predicated on the nature of a given carrier transmit drive signal waveform and its potential harmonics, the system may allow signal tuning/detuning so as to achieve a "best-case" resonant waveform.

Another aspect of the system of the present invention is to provide for on-the-fly and in-situ programming of a given RF tag. One such application is wherein a dentist utilizes the present invention to, as an example, take a molar x-ray, whereby the customary RINN SYSTEM device (used to both hold the x-ray film and assist in x-ray head alignment) has been replaced with an intelligent mouth x-ray film RF tag device. The system may then be configured to identify a "best-alignment" condition for communicating to the RF tag device, and/or for obtaining an x-ray. As the dentist's RF transponder indicates a critical alignment and/or valid "read" of the RF tag device, the dentist could enter certain information on a keyboard of which he or she wishes to be programmed into the intelligent mouth x-ray film RF tag device, such as a patient's name, date, and/or client number. That particular x-ray film RF tag device may remain permanently programmed and be directly traceable to that patient.

The system of the present invention may have other features, such as to indicate whether a given RF transponder is in a particular mode of operation, for example, data programming mode, tag detection/alignment mode, or idle mode. Other features of the system may include: 1) the capability of the RF transponder circuitry to provide indication of "best-alignment," without the need for utilizing customary alignment tools, devices, or procedures; and 2) to do so in a non-contact manner, wherein two net benefits and results are a) less complication for the dentist; and b) an enhanced comfort factor for dental patients.

Additional embodiments of the system of the present invention can be constructed such that the system may allow for those applications wherein a particular location must be reliably identified in three-dimensional space, and by a multiplicity of "points". For example, three RF tags may be used in an "x", "y" and "z" axis configuration that are configured to interface to/with a single or multiple frequency triple-coil RF transponder device also configured for "x", "y" and "z" axes. Further, the "x", "y" and "z" axes may or may not be relative to the predetermined positioning of the triple-coil RF transponder device or the predetermined positioning of the three RF tags. Such a system may be beneficial if the "x", "y" and "z" axes of the RF tags or RF transponder coils (or both) are required to be absolute or are allowed to reside at non-absolute angles/attitudes in free space. In this manner, the "x", "y" and "z" axes for either the RF tags or the triple-coils of the RF transponder may be utilized as fixed or variable. If one or the other components of the system (the RF tag or RF transponder coils, or both) are desired as variable, then the system offers significant repositionability and can be variably indexed about a full 360 degree locus. Accordingly, three RF tags and three RF transponders with one coil each could be employed so as to work as a single collective transducer apparatus or employed so as to function as three independently positionable transducer apparatus-sets. Each transducer apparatus-set may be configured to be positioned upon a separate predetermined or variable axis or plane. Alternatively, a single RF transponder device could be used, wherein it remains configured to utilize three or more carrier transmit/data receive coils of the same or differing sizes and carrier frequencies. Where such a 3-D function offers substantial benefit, is when used with various imaging technologies (for example, radiation treatments and laser or other surgeries) wherein medical equipment alignment and/or procedural site loci identification is important to both doctor and patient.

Furthermore, the system of the present invention may be configured with the capacity to allow for data programming of the RF tags for simple or specific utility, for example, patient processing. The programming may allow for such information as patient identification, allergy or medication warnings, past medical history, reason for admittance, date of admittance, procedure(s) to be performed, patient name, as well as patient age, date of birth, diet type, debilities, etc.

Additionally, the system of the present invention can be constructed in various sizes and with various features. Alternative embodiments of the system can be configured such that system may address such applications as latch-key kids and intelligent door lock systems (eliminating the need for physical keys); gardening/plant/crop/tree I.D. markers (which might also provide for feeding/care instructions); personal medication/allergy warning bracelets; patient medical history or processing tags; product history tags (with particular utility as regards warranty-period initialization or product tracking); newborn tracking/I.D. tags (which can assist in eliminating "swapped" newborn errors, as well as provide for accurate caretaker/parent access, or the setting off of alarms when an attempt to otherwise hold or remove a child has occurred); land boundary/corner markers (particularly useful with regards to certain mining "claims"); pet access tags (allowing a pet access to or from a home or yard at particular times of day, as an example); vehicle and vehicle compartment entry systems; computer access/denial systems; traveler luggage control/management systems; utility/gas/water line detection systems; ball park/entertainment/transit pass systems; medical diagnosis, imaging, and radiation systems; laser surgery systems; and of course, all manner of x-ray systems, to mention a few. Given such potential real-world applications, it is therefore the intended purpose of the present invention to offer a new, uncomplicated, utilitarian, reliable, and inexpensive yet intelligent and precise means of non-contact sensor alignment as pertains to RF tag devices and RF transponder devices, which herein together, now provide for a novel RFID transducer alignment system for critical-alignment as regards precision x-ray and medical applications, as well as those myriad applications wherein issues regarding "alignment" may or may not be deemed exacting.

Referring now to FIG. 1 and item 8000 in particular, the figure represents a physical system block diagram of an embodiment of an RFID transducer alignment system providing for an altogether new RFID application and market, and, the general enhancement of common RFID systems according to the present invention.

Referencing FIG. 1, item 1000, referred to herein as "RF transponder" and/or "RF transponder means", is at assembly caused to be attached to item 2000, referred to herein as "RF reader" and/or "RF reader means", by means of a predetermined cable apparatus, item 4000, referred to herein as "reader umbilical cable" and/or "reader umbilical cable means". Item 3000, referred to herein as "RF tag" and/or "RF tag means", remains the final subsystem component of the RFID transducer alignment system, but is in no way attached to any other component of or within the system.

Generally speaking, when items: 1000 (the RF transponder means), 2000 (the RF reader means) and 4000 (the reader umbilical cable means) have been assembled, and when item 1000 (the RF transponder means) is then enabled, by means of a predetermined power switch and applied power source, item 2000 (the RF reader means) will predeterminedly begin RF emissions, and at a predetermined frequency, of 100 kilohertz or greater, resulting in a radiated RF field of electromagnetic (EM) flux from item 2000 (the RF reader means).

When the RF tag means, item 3000, also constructed to oscillate at a predetermined frequency of 100 kilohertz or greater, and which frequency is ultimately caused to be near or identical of that of item 2000 (the RF reader means), and when brought within a predetermined distance of item 2000 (the RF reader means), the RF emissions of item 2000 (the RF reader means) will cause the LC tank circuit of item 3000 (the RF tag means) (more filly depicted in FIG. 4), to begin to self-oscillate, resulting in a radiated RF field of electromagnetic (EM) flux from item 3000 (the RF tag means).

As the LC tank circuit of the RF tag means, item 3000, begins to self-oscillate, internal power for the RF tag means, item 3000, is created by an internal power conditioning circuit, and ultimately, a serialized "data stream" is generated by an associated and integral microcontroller device means. The serialized data stream is applied to the LC tank circuit in a manner which then provides the effect of dampening the oscillations of the LC tank circuit.

Therefore, and as the LC tank circuit of the RF tag means, item 3000, begins to self-oscillate, RF emissions are predeterminedly created therefrom, which can be observed to be impressed with serialized data. In essence then, the RF emissions from the LC tank circuit of the RF tag means, item 3000, become modulated by the serialized data stream.

As the above occurs, the resonating RF emissions signal created by RF reader coil, 2002, of the RF reader means, 2000, now being impressed with a return RF emissions signal containing modulated serial data from the RF tag means, 3000, can be observed to have both: a reduced amplitude, and, to contain a representation of the modulated serialized data. The RF transponder, 1000, containing certain circuitry which can detect, filter, and amplify the serialized data, then transforms a resultant signal thereof into a viable and useable data stream signal, in effect reconstructing the original data stream as provided by the RF tag means, 3000.

The viable and useable data stream signal is then applied to, and read by, a microcontroller device within the RF transponder, 1000, and minimally predicated on: application and predetermined firmware, the RF transponder, 1000, then performs certain desired real-world functions; one of which, is that of indicating whether or not a critical alignment condition of the RF tag to the RF reader exists, and by various means, which include, but are not limited to: visual and/or audio means, and/or a computer apparatus, 6000, and/or, a printer apparatus, 7000.

Figure 2A:
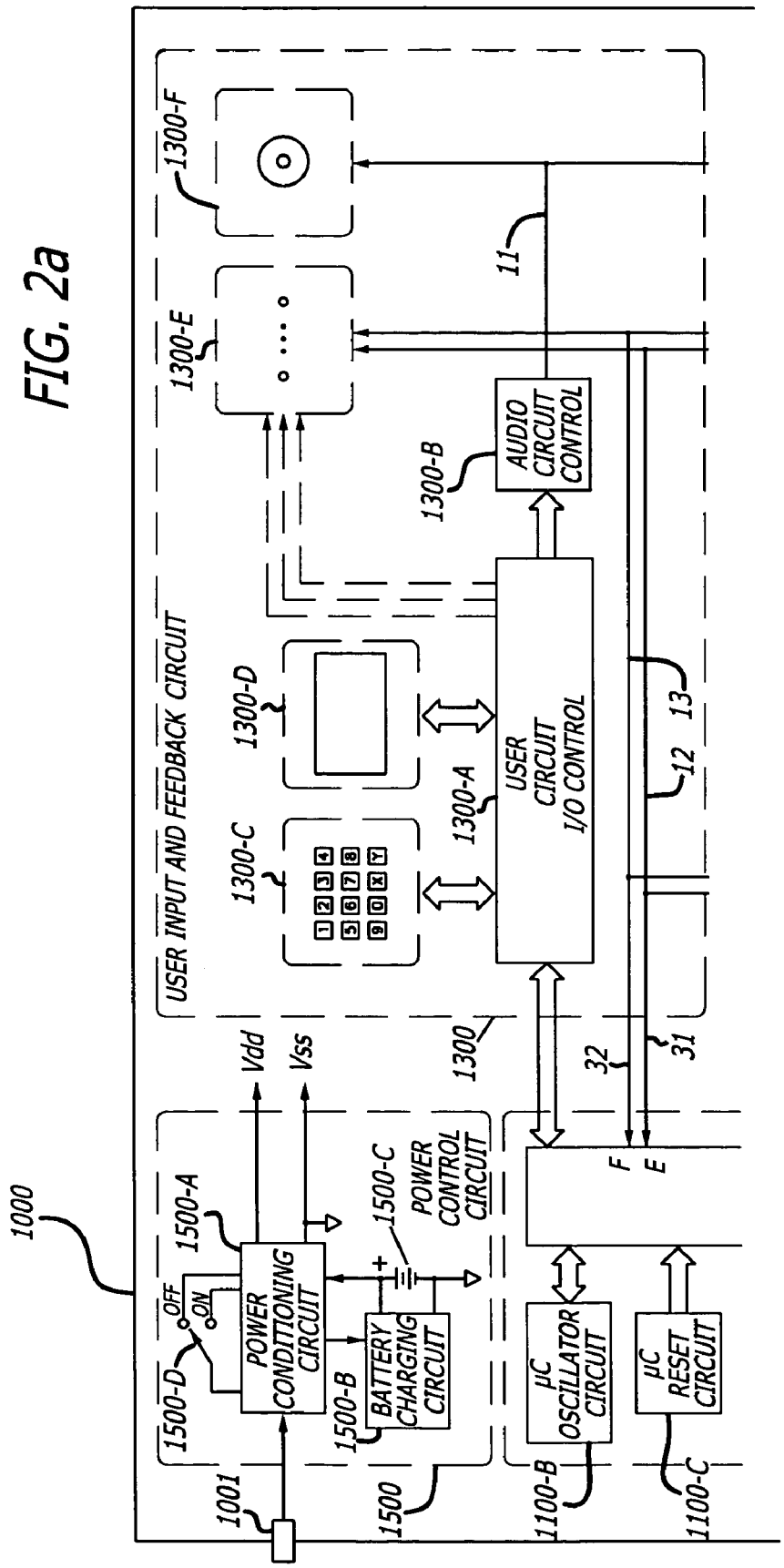
FIGS. 2a and 2b depict a subsystem block diagram of an embodiment of an RF transponder according to the present invention.
Figure 2B:
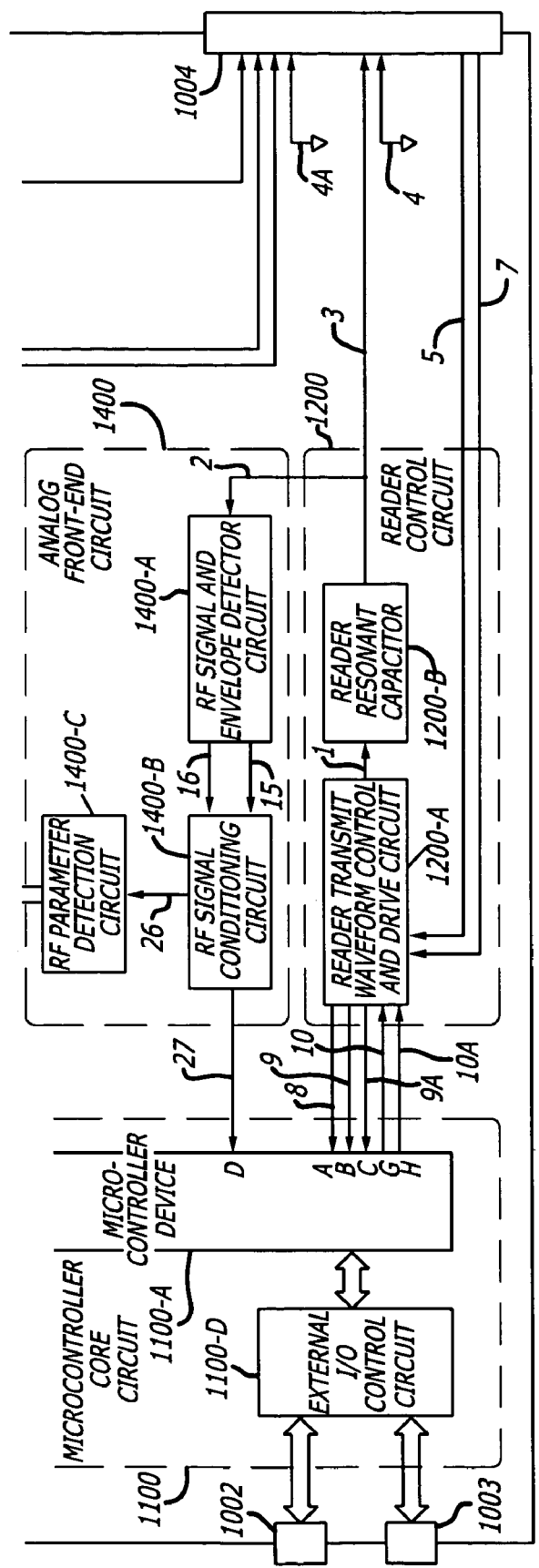

The following descriptions provide yet further detail with regard to FIG. 1, and, as relates to each main sub-system component of the present invention:

Now referencing FIGS. 2A and 2B, one will note multiple circuit sections within the block identified as 1000, "RF transponder," wherein there is illustrated the five main circuit components to the RF transponder means, identified as: power control circuit, 1500, microcontroller core circuit, 1100, user input and feedback circuit, 1300, analog front-end, 1400, and, reader control circuit, 1200.

Three of the five main circuit components, noted as: power control circuit, 1500, microcontroller core circuit, 1100, and user input and feedback circuit, 1300, remain entirely non-complex, and can be constructed by various means, in various ways, to provide the functions indicated. Intensive detail therefore, is not felt required of these the three main circuit components, thusly, abbreviated descriptions thereof will more than adequately suffice, and will indeed follow.

However, and as may not be clear to those skilled in the art, the last two of the five main circuit components, noted as: analog front-end, 1400, and, reader control circuit, 1200, remain not only as essential aspects of the present invention, but remain somewhat complex in nature. Therefore these last two main circuit components require more explicit detail for fully understanding the present invention, and such detail will also follow.

To begin, and referencing both FIGS. 2 and 1, a predetermined connector apparatus, 1001, accommodates a predetermined applied external power source, 5000, wherein at least one predetermined power potential may generally be applied to the power control circuit, 1500, and specifically, to the power conditioning circuit, 1500-A, whereby one or more predetermined voltage potentials may be created for use by the remaining circuits of the "RF transponder", 1000.

The power conditioning circuit, 1500-A, provides for an applied power switching device, 1500-D, allowing for application control of the applied power source, whether that source be internal or external, to the remainder of the power conditioning circuit, 1500-A. Also a part of the power control circuit, 1500, and as an option to utilizing the applied external power source, 5000, a predetermined battery device, 1500-C, may be used, if desired, being particularly beneficial in certain hand-held embodiments and/or applications of the present invention.

In those applications where external power source backup, or, occasional freedom from an external power source is desired, provisions for a battery charging circuit, 1500-B, is additionally made available, to predeterminedly charge the predetermined battery device, 1500-C, during those occasions when appropriate to do so, and, when the applied external power source, 5000, is made available.

In whole then, the power control circuit, 1500, may provide for either or both: an externally applied power source, and/or, an internally supplied power source, and, wherein ultimately the predetermined voltage potentials to operate the whole of the RF transponder means is created and provided for.

The microcontroller core circuit means, 1100, provides for: a predetermined microcontroller device means, 1100-A, a microcontroller (μC) oscillator circuit, 1100-B, a microcontroller (μC) reset circuit, 1100-C, and an external I/O control circuit, 1100-D.

The predetermined microcontroller device means, 1100-A, provides for multiple functional means, not limited to, but including those functional means of: certain I/O ports and/or pins, internal RAM and ROM or $E^2$ memory, etc., an internal clock generator, reset control, at least one internal timer, and perhaps, an A/D converter.

The microcontroller (μC) oscillator circuit, 1100-B, may be predeterminedly composed of a predetermined crystal oscillator device and two capacitor devices, typically providing means not only for enhanced oscillation stability over temperature, but for a broad range of frequencies at which the microcontroller device means, 1100-A, may operate, or, remain (potentially) constructed of a resistor device and a capacitor device in series, providing means for reduced oscillation stability over temperature, and, a minimum frequency at which the microcontroller device means, 1100-A, may operate.

The microcontroller (μC) reset circuit, 1100-C, may be predeterminedly constructed of a resistor device and a capacitor device in series, provides means for the microcontroller device means, 1100-A, to note when adequate operational power is dependably available, as well as allows the microcontroller device means, 1100-A, to note when to reset various internal registers in preparation for proper operation to occur.

The external I/O control circuit, 1100-D, may be predeterminedly constructed of simple logic-gate devices, and/or, communications port function-specific I/O devices, such as serial or parallel communications devices, wherein the microcontroller device means, 1100-A, may effect communication to and/or with certain external devices, such as a remote printer apparatus, 7000, and/or a remote computer apparatus, 6000, per predetermined external connector apparatus' 1003 and 1002, respectively.

User input and feedback circuit means, 1300, provides for: a predetermined user keyboard apparatus means, 1300-C, a predetermined user LCD (or other "like" display) apparatus means, 1300-D, predetermined LED (light emitting diode) display means, 1300-E, a predetermined audio control circuit means, 1300-B, a predetermined audio device means, 1300-F, and, a predetermined user input/output (I/O) control circuit means, 1300-A.

The predetermined user I/O control circuit means, 1300-A, in effect a signal multiplexer, is constructed so as to allow means wherein certain discrete logic signals and/or data bus signals, etc., can be steered to or from, and between: the microcontroller device means, 1100-A, and: the predetermined user keyboard apparatus means, 1300-C, predetermined user LCD (or other "like" display) apparatus means, 1300-D, predetermined LED (light emitting diode) display means, 1300-E, and, predetermined audio control circuit means, 1300-B.

Further, the predetermined user I/O control circuit means, 1300-A, may be generally constructed of simple logic gate devices and/or one or more (perhaps tri-state-able) 8-bit latch and/or bus circuit devices, so as to provide means for the microcontroller device means, 1100-A, to interface to and/or with the: predetermined user keyboard apparatus means, 1300-C, predetermined user LCD (or other "like" display) apparatus means, 1300-D, predetermined LED (light emitting diode) display means, 1300-E, and, predetermined audio control circuit means, 1300-B, when need be, and, with the benefit of requiring only a minimized quantity of I/O and or port pins on the microcontroller device means, 1100-A, to do so.

The predetermined user keyboard apparatus means, 1300-C, enabled by the user I/O control circuit means, 1300-A, and generally constructed of two or more push button switches, provide means for a given user of the present invention to input certain predetermined data, instructions, and/or commands, etc., to the microcontroller device means, 1100-A.

The predetermined user LCD (or other "like" display) apparatus means, 1300-D, enabled by the user I/O control circuit means, 1300-A, provides means for a given user to note: inputted user data or instructions or commands, etc., to the microcontroller device means, 1100-A, as well as: obtain feedback related to: user-inputted information, as well as: certain other data and/or predetermined operational parameters as may be provided by the RF transponder, 1000, and/or, the RF transducer alignment system, 8000.

Further, the predetermined user LCD (or other "like" display) apparatus means, 1300-D, may also provide additional means required for a backlighting function, particularly beneficial for RF transducer alignment system operation in dimly lit areas.

The predetermined LED (light emitting diode) display means, 1300-E, enabled by the user I/O control circuit means, 1300-A, and composed of one or more LED devices, and, a current limiting series resistor device for each installed LED device, provides quick feedback means for a given user, whereby one can note: certain predetermined operational parameters of the RF transponder, 1000, and/or, the RF transducer alignment system, 8000, such as: when a "ready to operate" state has been established, or when a given RF tag is detected, and/or, yet other parametric nuances as required by application or desire.

Figure 3:
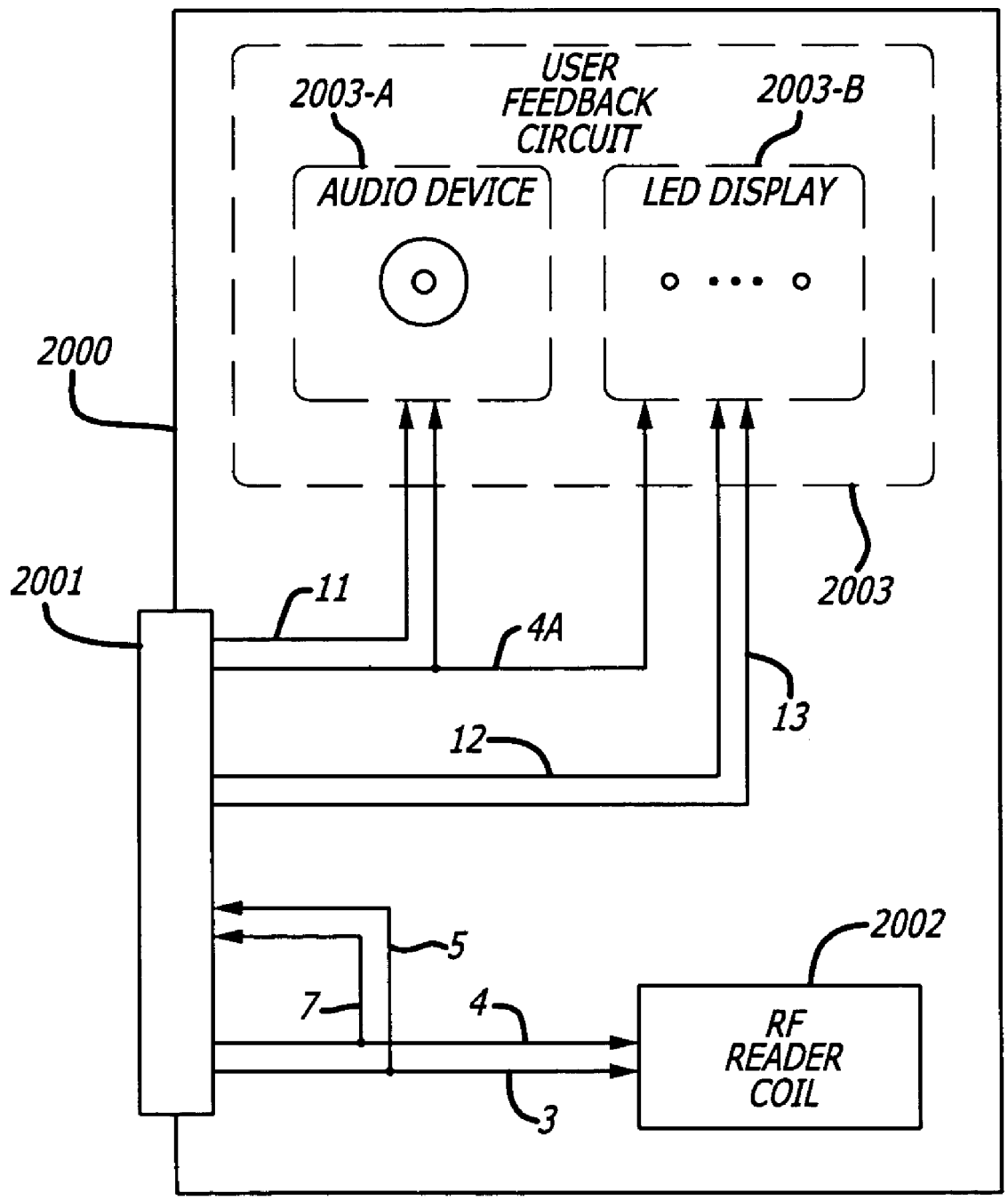
FIG. 3 depicts a subsystem block diagram of an embodiment of an RF reader according to the present invention.

Further, one or more certain predetermined signals of the predetermined LED (light emitting diode) display means, 1300-E, may additionally be passed on to a predetermined connector device, 1004, so that the signals may then be passed through the reader umbilical cable means, 4000, to the RF reader means, 2000, and now referencing FIG. 3, through a predetermined connector apparatus, 2001, to user feedback circuit, 2003, and ultimately, to LED display means, 2003-B, also of FIG. 3.

Referring again to FIG. 2, the predetermined audio control circuit means, 1300-B, enabled by the user I/O control circuit means, 1300-A, may be composed of a simple FET transistor, or like device, or, a gated tone and/or voice generator circuit, of which, and in either case, a predetermined signal thereof is predeterminedly and ultimately passed to the audio device means, 1300-F, so as to predeterminedly create an audibly noted source of feedback for a given user of the present invention, and, as may additionally concern specific system operation or function and/or parameter detection.

The audio device means, 1300-F, may be comprised of a standard speaker element, or even, a piezo device.

Further, a predetermined signal of the audio control circuit means, 1300-B, may additionally be passed on to a predetermined connector device, 1004, so that the signal may then be passed through the reader umbilical cable means, 4000, to the RF reader means, 2000, and now referencing FIG. 3 again, through a predetermined connector apparatus, 2001, to user feedback circuit, 2003, and ultimately, to audio device means, 2003-A, also of FIG. 3.

Referencing FIG. 2 once again, and as ought now be clear at this juncture, we have discussed the three the non-complex circuit components of the RF transponder means, 1000, to wit:

The power control circuit means, 1500, both receives and applies those voltage potential means necessary for proper operation of the RF transponder means, 1000; the microcontroller core circuit means, 1100-A, provides the intelligence and means to allow desired functionality of the RF transponder means, 1000; and, The user input and feedback circuit means, 1300, provides means allowing intimate user control of, and feedback from, the RF transponder means, 1000.

Referring now to FIGS. 3 and 1, we discuss the RF reader means, 2000. The RF reader means, 2000, is composed of a predetermined connector apparatus, 2001, which allows for applying certain predefined circuit signals from the RF transponder means, 1000, to the RF reader means, 2000, as well as for applying certain predefined circuit signals from the RF reader means, 2000, to the RF transponder means, 1000; an RF reader coil, 2002; and a user feedback circuit, 2003.

Input signal 11, a third applied signal, carries one or more predefined waveforms and/or frequencies, which become audibly notable as sound, when presented to a first predefined pin of item 2003-A, a predetermined audio device, of user feedback circuit, 2003. The audio device means, 2003-A, may as well be comprised of a standard speaker element, or a piezo device.

Input signal 12, a fourth applied signal, is presented to a first predefined pin of a first LED device of item 2003-B, of user feedback circuit, 2003, to indicate RF tag detection has occurred.

Input signal 13, a fifth applied signal, is presented to a first predefined pin of a second LED device of item 2003-B, of user feedback circuit, 2003, to indicate that a valid data stream signal has been detected.

Input signal 4A, a sixth applied signal, is presented to the remaining and second predefined pins of: the predetermined audio device, 2003-A, the first LED device of item 2003-B, and finally, the second LED device of item 2003-B, all of user feedback circuit, 2003, providing for a second circuit ground signal.

Input signal 3, a first applied signal, composed of a predetermined frequency when active, is presented to a first predefined lead of an RF reader coil apparatus, 2002, of RF reader means, 2000, as means to allow for eventual resonant oscillation of the RF reader coil apparatus, 2002. As the RF reader coil apparatus, 2002, then responds to the applied input signal, 3, a first EM field of flux, and carrier transmit EM field of flux signal, is created by the RF reader coil apparatus, 2002.

Output signal 5, a first return signal, is presented to the predetermined connector apparatus, 2001, as means to allow for monitoring the eventual resonant oscillations of the RF reader coil apparatus, 2002, by the RF transponder means, 1000.

Input signal 4, a second applied signal, is presented to a second predefined lead of an RF reader coil apparatus, 2002, of RF reader means, 2000, providing for a first circuit ground signal.

Output signal 7, a second return signal, is presented to the predetermined connector apparatus, 2001, as means to allow for monitoring the presence of the RF reader coil apparatus, 2002, within the RF transducer alignment system, 8000, by the RF transponder means, 1000.

Figure 4:
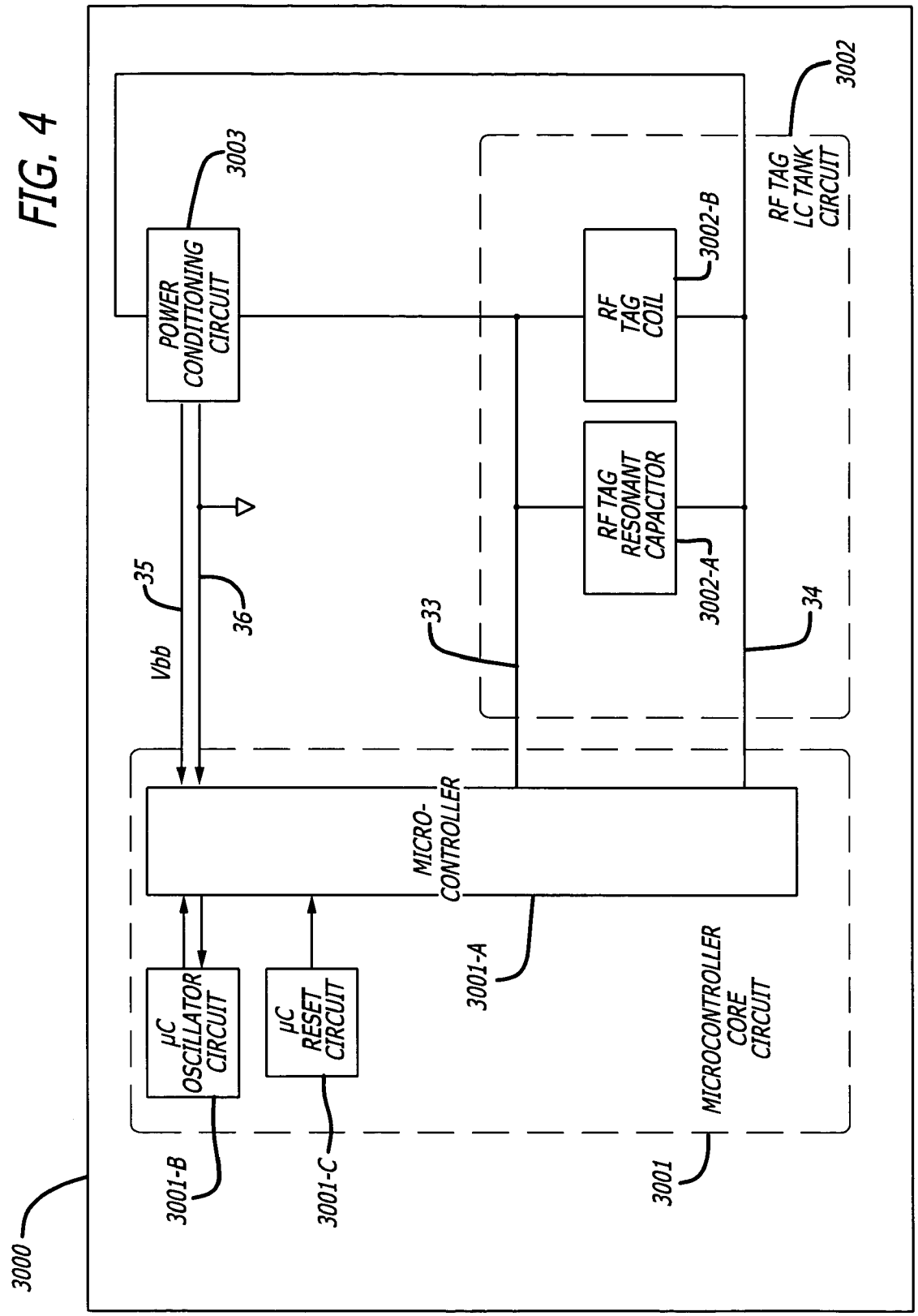
FIG. 4 depicts a subsystem block diagram of an embodiment of an RF tag according to the present invention.

Referring now to FIGS. 4 and 1, we discuss the RF tag means, 3000. The RF tag means, 3000, is composed of a predetermined microcontroller (µC) core circuit, 3001, fabricated by means of: a predetermined µC oscillator, 3001-B, a predetermined µC reset circuit, 3001-C, and a predetermined microcontroller device means, 3001-A; a predefined RF tag LC tank circuit, 3002, fabricated by means of a predetermined RF tag resonant capacitor device, 3002-A, and a predefined RF tag coil apparatus, 3002-B; and finally, a predetermined power conditioning circuit, 3003.

The RF tag means, 3000, is a stand-alone apparatus which requires no on-board or attached power source for operation. As indicated earlier, power for the RF tag means, 3000, is obtained when the RF tag means, 3000, is brought within close proximity of a first radiated EM field of flux, as would typically be provided by the RF reader means, 2000, such that the RF tag LC tank circuit, 3002, becomes impressed with the first radiated EM field of flux, which then excites the RF tag LC tank circuit, 3002, into self-oscillation, which as a result, produces a localized second EM field of flux.

The second EM field of flux, produced by the RF tag LC tank circuit, 3002, is then radiated from the RF tag LC tank circuit, 3002, and the RF tag means, 3000.

A portion of the energy created by the second EM field of flux, produced by the RF tag LC tank circuit, 3002, is then applied to the power conditioning circuit, 3003, composed of a predetermined rectifier circuit and capacitor device, whereby: a second internal signal, and circuit ground signal, 36, is created; and, a predetermined voltage potential, of a D.C. nature, is created, which is then applied, via a first internal signal, 35, to the microcontroller device means, 3001-A, providing for operational power.

When the microcontroller device means, 3001-A, predefinedly asserts the predetermined voltage potential to be stable, the microcontroller device means, 3001-A, predeterminedly begins to dampen the oscillations produced by the RF tank LC circuit, 3002, by such means as applying a predefined and "stored" data stream signal to the base of an internal FET transistor device, thereby enabling the FET, whose drain and source pins are, effectively, placed across third and fourth internal signals, 33 and 34, respectively, which by virtue of physical attachment and the enabled FET, impresses the second EM field of flux, produced by the RF tag LC tank circuit, 3002, with the "stored" data stream signal, culminating in: a modulated second EM field of flux, and, a data transmit/return EM field of flux signal.

Because the construction and operation of items 3001-B and 3001-C have been generally described earlier, and as related to the RF transponder means, items 1100-B and 1100-C, respectively, repeat discussion is felt unnecessary. Suffice it to say: item 3001-B provides means by which the microcontroller device means, 3001-A, might obtain a system clock for operation, and that item 3001-C provides means by which the microcontroller device means, 3001-A, might obtain a reset signal, so as to predeterminedly begin operation.

Now, we begin examination of reader control circuit means, 1200, and analog front-end circuit means, 1400, the remaining two, and more complex, circuit components of the RF transponder means, 1000.

Figure 5:
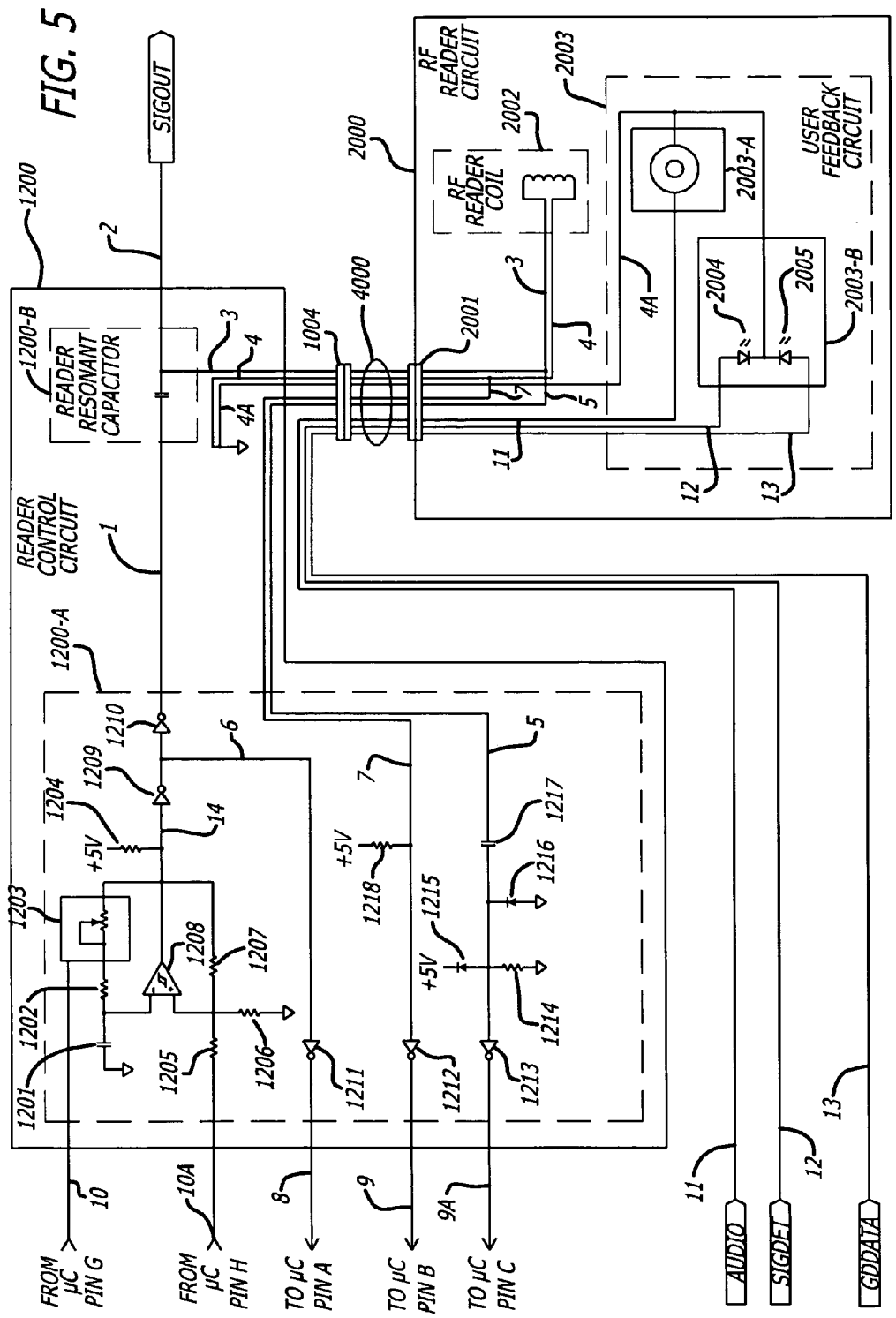
FIG. 5 depicts a portion of a schematic diagram of an embodiment of the RFID transducer alignment system according to the present invention.

Referring to FIG. 2 for an overview, and referencing FIG. 5 for clarity of this section: One will note item 1200, the reader control circuit means, is composed of reader transmit waveform control and drive circuit means, 1200-A, and, reader resonant capacitor, 1200-B.

The reader transmit waveform control and drive circuit means, 1200-A, provides means whereby a predetermined square wave signal, in this embodiment, is generated by item and circuit predetermined component 1208, a comparator device, and, predetermined items and circuit components 1201 through 1207, which together provide for the reader transmit waveform control portion of the reader transmit waveform control and drive circuit means, 1200-A.

It remains the comparator device, 1208, is gated, and thus enabled or disabled, by means wherein resistor and item 1205 is made responsive to a selected output pin and signal, 10A, from the microcontroller device means, 1100-A, wherein a first and left lead and input to resistor and item 1205, is alternatively, and predeterminedly, pulled logically HI or LO.

Predetermined resistors and items 1205 and 1206 provide means to create a center voltage potential of ½ of the applied circuit voltage, in this embodiment, of 2.5 volts D.C., when the first and left lead and input to resistor and item 1205, is pulled logically HI. The center voltage potential, for example, 2.5 volts, becomes the baseline for oscillation to occur about the comparator device, 1208. When the first and left lead and input to resistor and item 1205, is pulled logically LO, the comparator device, 1208, is disabled from oscillating.

If gating the comparator device, 1208, is not required for a particular application and/or embodiment, the first and left lead and input to resistor and item 1205, may be tied directly to +5V instead.

Predetermined resistors and items 1202 and 1203 and predetermined capacitor and item 1201, provide means for actual oscillation about the comparator device, 1208, to occur.

As illustrated, resistor and item, 1203, is programmably made to be variable, wherein actual resistance value of resistor and item 1203 is intimately controlled by pin G, noted as signal 10, from the microcontroller device means, 1100-A, and thus ultimately provides for variation in the oscillation frequency about the comparator device, 1208, which, based on the components illustrated, allows for a oscillation and frequency range of approximately: 113 kilohertz, to 165 kilohertz. For this embodiment it should be noted the selected frequency of oscillation was set to 119.5 kilohertz.

As well of note, resistor and item 1203 can alternatively be replaced, and with a manual variable-resistor device.

Now, since circuit component and item 1208, the comparator device, allows only for an open-collector transistor output, which provides for a logical LO state and output signal when turned on, predetermined resistor and item 1204, a pull-up device, must be installed to accommodate a logical HI state and output signal when the open-collector transistor is turned off, which collectively then, provides for the required two-state duty cycle.

Thus, the collective junction of the open-collector transistor output of circuit component and item 1208, the comparator device, and the predetermined resistors and items 1204, 1203, and 1207, provide not only for the required two-state duty cycle, but an oscillating circuit signal, 14, of 119.5 kilohertz, having the form of a square wave.

For alternative embodiment sake, understand circuit components 1201 through 1208 can be wholly replaced by a predetermined crystal clock oscillator circuit and a predetermined divide-by-X circuit, as an example, which together, can also provide for a predetermined square wave frequency output. However, slight frequency changes, if desired, are limited and made more difficult, in that by the very nature of such the circuitry: only fundamental harmonics of the crystal oscillator frequency can be easily realized; to wit: f f/2, f/3, f/4, etc.

As an example: the output of a 4 megahertz crystal oscillator circuit applied to a "straight-forward" divide-by 32 logic device or circuit, will easily provide for a 125 kilohertz square wave output, but not easily accommodate providing for a 119.5 kilohertz square wave output. Neither will the logic device or circuit, set to divide by 16, or divide by 64, accommodate providing for a 119.5 kilohertz square wave output.

To continue: The square wave signal, 14, is then applied to the input of predetermined circuit component and item 1209, an inverter device, which inverts the square wave signal. This resultant signal, 6, is then applied to the inputs of two following predetermined inverter devices, 1210, and 1211, so as to buffer the resultant signal, 6, and perform a signal phase correction.

The output of circuit component and item 1211, noted as signal 8, is then fed back to a predetermined input, pin A, of the microcontroller device means, 1100-A, so as to provide means whereby the oscillation frequency of the circuit component and item 1208 can be monitored.

Circuit component and item 1210, and its output, noted by signal 1, together provide for the reader transmit waveform drive portion of the reader transmit waveform control and drive circuit means, 1200-A, whereby the output signal, 1, is fed forward and applied to a first pin of a predetermined reader resonant capacitor, 1200-B.

The remaining and second pin of the predetermined reader resonant capacitor, 1200-B, is ultimately made to connect to a first lead of a predetermined RF reader coil, 2002, by means of circuit signal 3 and predetermined connector apparatus, 2001, whereupon oscillations of the predetermined frequency can be observed when the remaining and second lead of the RF reader coil, 2002, is connected to circuit ground by means of circuit signal 4 and predetermined connector apparatus, 2001.

Output signal 2, identified by the nomenclature: "SIGOUT", also attached to the remaining and second pin of the predetermined reader resonant capacitor, 1200-B, provides means by which the oscillations of a predetermined frequency upon circuit signal 3, can be passed on to that circuitry identified as analog front-end, 1400, of FIG. 2, and in particular, to the anode of diode and item 1401, of FIG. 6, of a signal detection circuit, 1400-A, which will collectively be discussed shortly.

As expected, the output signal 2, which is exactly the same as the circuit signal 3, is fundamentally a sine wave, and remains of an alternating voltage potential which greatly exceeds that of the reader transmit waveform drive signal, 1. Component values and resonance factors of both: the predetermined reader resonant capacitor, 1200-B, and the predetermined RF reader coil, 2002, working in synchronicity with each other, and, depending on the frequency of oscillations supplied by signal 14, together provide means for the amplitude exacerbation observed of the output signal 2.

In fact, peak-to-peak voltages of greater than 150 volts can be observed of output signal 2 when maximum resonance is sought. However, and for best operation of the present invention, in this embodiment, the frequency of oscillations supplied by signal 14 are generally made to be detuned by about 7% from the inherently derived resonant frequency, as calculated by standard LC resonance equation [ie: ½*PI*square rootLC] and the actual values of the predetermined reader resonant capacitor, 1200-B, and the predetermined RF reader coil, 2002, which, and also as expected, somewhat reduces the amplitude of the circuit signal 3 and the output signal 2, yet does not affect or negatively impact operation of the transponder means, 1000, in any way.

There is a portion of FIG. 5 which contains a schematic of the RF reader circuit, 2000, which therein provides for a multiplicity of input/applied and output/return signals at predetermined connector apparatus, 2001, as addressed earlier in this section. As to understanding FIG. 5 in more detail:

Internal circuit signal, 7, of the RF reader circuit, 2000, provides means whereby the RF transponder means, 1000, might monitor the presence of circuit signal 4 and the RF reader circuit, 2000, and particularly, the presence of the RF reader coil apparatus, 2002, so as to typically either: note and indicate the lack of a main sub-system component, and so at a minimum, predeterminedly disable the comparator device, 1208, or otherwise, proceed into predefined normal operations, and predeterminedly enable the comparator device, 1208.

If the reader umbilical cable apparatus, 4000, is attached to item 1004, a predetermined connector apparatus, and component of the reader control circuit, 1200, AND if the RF reader circuit, 2000, is attached to the reader umbilical cable apparatus, 4000, internal circuit signal, 7, of the RF reader circuit, 2000, will be presented to the reader control circuit, 1200, and to resistor component and item 1218, as well as to the input of circuit component and inverter device, 1212. The output of circuit component and inverter device, 1212, will then be forced logically HI, indicating to the microcontroller devices means, 1100-A, by means of signal 9 being presented to μC input pin B, that the RF reader circuit, 2000, is indeed present.

However, if the reader umbilical cable apparatus, 4000, is not attached to item 1004, a predetermined connector apparatus, and component of the reader control circuit, 1200, OR, if the RF reader circuit, 2000, is not attached to the reader umbilical cable apparatus, 4000, internal circuit signal, 7, of the RF reader circuit, 2000, will not be presented to the reader control circuit, 1200, and to resistor component and item 1218, as well as to the input of circuit component and inverter device, 1212. In this case, the output of circuit component and inverter device, 1212, will then be forced logically LO, indicating to the microcontroller devices means, 1100-A, by means of signal 9 being presented to μC input pin B, that the RF reader circuit, 2000, is absent.

As well, internal circuit signal, 5, of the RF reader circuit, 2000, provides means whereby the RF transponder means, 1000, might monitor the presence of circuit signal 3 and the eventual resonant oscillations of the RF reader coil apparatus, 2002, of RF reader circuit, 2000, so as to typically: note and indicate the lack of the eventual resonant oscillations, andlor, note and indicate the frequency of the eventual resonant oscillation.

If the reader umbilical cable apparatus, 4000, is attached to item 1004, a predetermined connector apparatus, and component of the reader control circuit, 1200, AND, if the RF reader circuit, 2000, is attached to the reader umbilical cable apparatus, 4000, internal circuit signal, 5, of the RF reader circuit, 2000, will be presented to the reader control circuit, 1200, by means of a first lead of circuit component and capacitor device, 1217, wherein the circuit component and capacitor device, 1217, acts to A.C. couple the internal circuit signal, 5, of the RF reader circuit, 2000, to the reader control circuit, 1200.

The second and remaining lead of circuit component and capacitor device, 1217, passes a portion of the internal circuit signal, 5, applied to the first lead of circuit component and capacitor device, 1217, as a resultant signal, on to: predetermined circuit component and diode device, 1216, and the cathode thereof; and predetermined circuit component and diode device, 1215, and the anode thereof; and, to predetermined circuit component and resistor device, 1214.

When the eventual resonant oscillations from the RF reader coil apparatus, 2002, are present, the circuit components and diode devices, 1215 and 1216, act to clip any excess and undesired voltage peaks from the resultant signal provided for by means of the second lead of the circuit component and capacitor device, 1217.

In this instance, the circuit component and resistor device, 1214, acts to reference the resultant signal provided for by means of the second lead of the circuit component and capacitor device, 1217, to circuit ground.

The resultant signal, provided for by means of the second lead of the circuit component and capacitor device, 1217, is then applied to the input of predetermined circuit component and inverter device, 1213, whereby the output of circuit component and inverter device, 1213, will invert the resultant signal, and pass the inverted resultant signal on to the predetermined microcontroller devices means, 1100-A, by means of signal 9A being presented to μC input pin C.

However, if the reader umbilical cable apparatus, 4000, is not attached to item 1004, a predetermined connector apparatus, and component of the reader control circuit, 1200, OR, if the RF reader circuit, 2000, is not attached to the reader umbilical cable apparatus, 4000, internal circuit signal, 5, now an open circuit, will still be presented to the reader control circuit, 1200, by means of a first lead of circuit component and capacitor device, 1217, but since no signal of oscillation will be present, the circuit component and capacitor device, 1217, becomes in effect, an open circuit as well.

Therefore, and without circuit component and resistor device, 1214, being in place, the second lead of circuit component and capacitor device, 1217, and its voltage potential, would be considered: "floating"; ergo: remaining both: unreferenced, and undesired. Thusly, in this instance, the circuit component and resistor device, 1214, acts to reference the input of circuit component and inverter device, 1213, to circuit ground.

In addition, circuit components and diode devices, 1215 and 1216, also, in essence, become open circuits.

The effect of having no resultant signal, as would otherwise normally be provided for by means of the second lead of the circuit component and capacitor device, 1217, is that the input of circuit component and inverter device, 1213, now reference to circuit ground, by means of the circuit component and resistor device, 1214, provides a steady state logical HI signal as an output, to the microcontroller devices means, 1100-A, by means of signal 9A being presented to μC input pin C.

Certain undiscussed circuit signals of FIG. 5 and the RF reader circuit means, 2000, identified as: circuit signal 11 and by the nomenclature: "AUDIO"; circuit signal 12 and by the nomenclature: "SIGDET"; and, circuit signal 13 and by the nomenclature: "GDDATA", shall now be elaborated upon.

Figure 6:
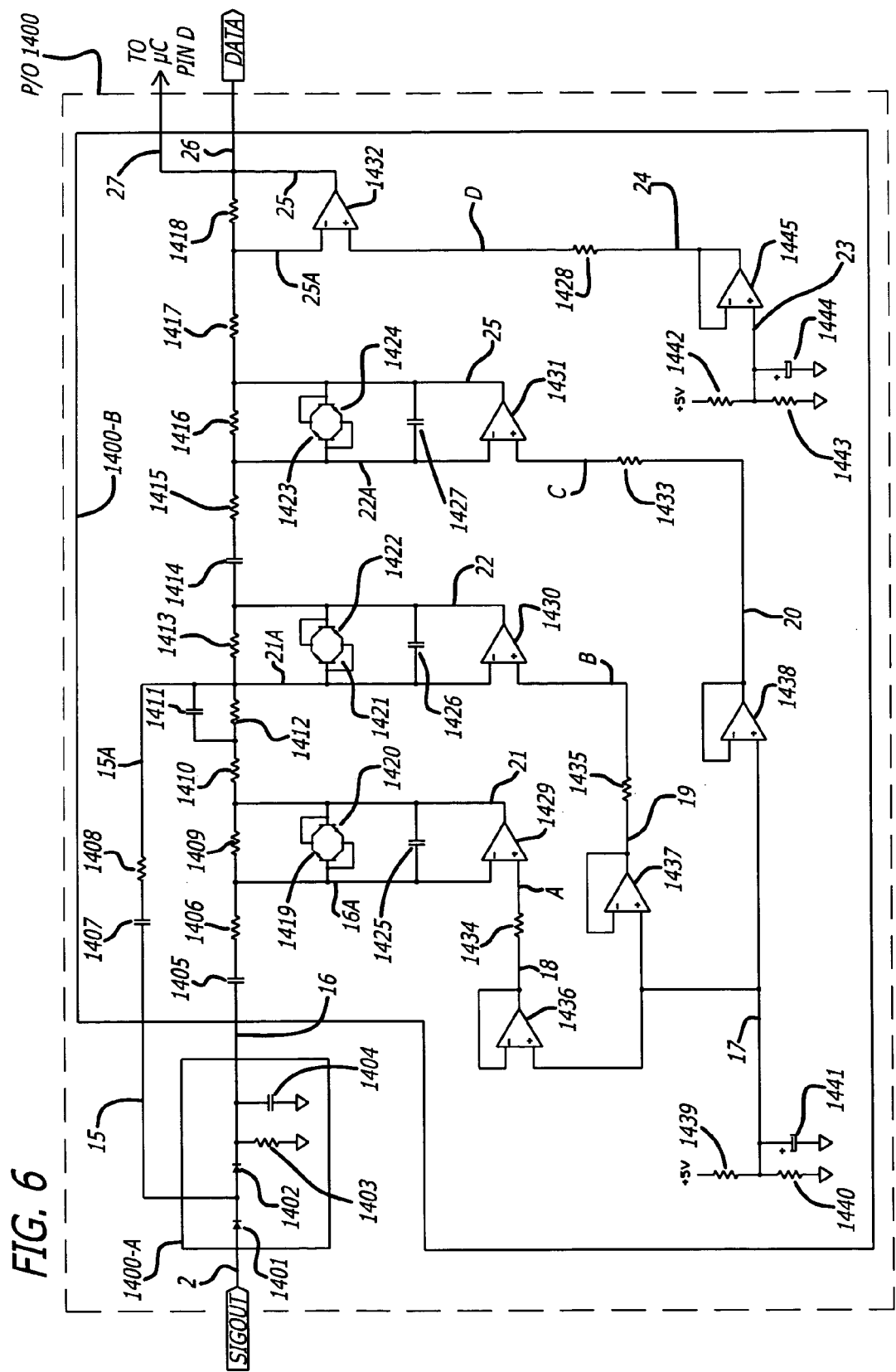
FIG. 6 depicts a portion of a schematic diagram of an embodiment of the RFID transducer alignment system according to the present invention.

The origin of the above three circuit signals is to be found in FIG. 6, which has yet to be discussed, however, these signals have been somewhat addressed earlier, when the RF reader circuit means, 2000, was described, thus for the moment, suffice it to say:

The input circuit signal 11, identified by the nomenclature: "AUDIO", is caused to be presented to the RF reader circuit means, 2000, in part, by means of the predetermined connector apparatus, 2001, and ultimately, to a first predefined pin of circuit component and predetermined audio device, 2003-A. The input circuit signal 11, will predeterminedly be either: at circuit ground potential, providing for "off" functionality of the circuit component and predetermined audio device, 2003-A, OR, apply one or more predefined waveforms and/or frequencies, which become audibly notable as sound, when presented to the first predefined pin of item 2003-A, the predetermined audio device, of user feedback circuit, 2003, thus providing means control and/or activate the audio device and item 2003-A, providing in addition, for "on" functionality; and The input circuit signal 12, identified by the nomenclature: "SIGDET", is caused to be presented to the RF reader circuit means, 2000, by means of the predetermined connector apparatus, 2001, and ultimately, to a first predefined pin of circuit component and predetermined first LED device, 2004. The input circuit signal 12, will predeterminedly be either: held at +5V, if SIGDET is active, or, apply the circuit ground potential, if SIGDET is not active, to the first predefined pin of the LED and item 2004, or user feedback circuit, 2003, thus providing means to toggle the LED and item 2004 on and off, respectively; and The input circuit signal 13, identified by the nomenclature: "GDDATA", is caused to be presented to the RF reader circuit means, 2000, by means of the predetermined connector apparatus, 2001, and ultimately, to a first predefined pin of circuit component and predetermined second LED device, 2005. The input circuit signal 13, will predeterminedly be either: held at +5V, if GDDATA is active, or, apply the circuit ground potential, if GDDATA is not active, to the first predefined pin of the LED and item 2005, of user feedback circuit, 2003, thus providing means to toggle the LED and item 2005 on and off, respectively.

The remaining undiscussed circuit signals of FIG. 5 and the RF reader circuit means, 2000, shall now be addressed, to wit:

Circuit signal 4A, is presented to the remaining and second predefined pins of: the predetermined audio device, 2003-A, the first LED device, 2004, of item 2003-B, and, the second LED device, 2005, of item 2003-B, all of user feedback circuit, 2003, providing for a second circuit ground signal of and to, the RF reader circuit means, 2000, by means of predetermined connector apparatus, 2001.

Circuit signal 3, applied by means of the predetermined connector apparatus, 2001, and composed of one or more predetermined frequencies, at a minimum, when active, is presented to a first predefined lead of a predetermined RF reader coil apparatus, 2002, of RF reader circuit means, 2000, as means to allow for eventual resonant oscillation of the RF reader coil apparatus, 2002. As the RF reader coil apparatus, 2002, responds to an actively applied input signal, 3, a first EM field of flux, and carrier transmit EM field of flux signal, is created by the RF reader coil apparatus, 2002.

We at last consider FIG. 6, which illustrates a first partial drawing of the analog front-end, 1400, and which is comprised of: RF signal and envelope detector circuit, 1400-A, and, RF signal conditioning circuit, 1400-B.

The output signal 2, first illustrated in FIG. 5, and identified by the nomenclature: "SIGOUT", is applied to FIG. 6, and in particular, to the anode of diode and item 1401, the first circuit component and signal rectifier of the RF signal and envelope detector circuit, 1400-A.

The cathode of the diode and item 1401, noted as raw circuit signal 15, is then applied to the anode of diode and item 1402, a second circuit component and signal rectifier of the RF signal and envelope detector circuit, 1400-A, as well as is applied to predetermined capacitor and circuit component and item 1407.

The cathode of the diode and item 1402, is then applied to predetermined circuit components and items: 1403, a predetermined resistor device, and 1404, a predetermined capacitor device, whereby a resultant detected signal, 16, is both created and referenced to circuit ground. The resultant detected signal, 16, remains considerably reduced in amplitude from the applied output signal 2, and is comprised, in part, of a partially modulated carrier transmit signal.

Pausing briefly: Recall now that as the RF reader means, 2000, is brought within close proximity of the RF tag means, 3000, (or vise versa), the RF reader coil apparatus, 2002, becomes impressed with the data-modulated return EM field of flux signal provided by the RF tag means, 3000. As this occurs then, the data-modulated return EM field of flux signal provided by the RF tag means, 3000, appears in part at the circuit signals 3 and 2 and first lead of the RF reader coil apparatus, 2002, as backscatter.

Continuing: The resultant detected signal, 16, displays a multiplicity of frequency components, comprised at a minimum of: the carrier transmit signal, of 100 kilohertz or greater, as provided by the RF reader coil apparatus, 2002; the data receive signal, comprised of 100 kilohertz or greater, being modulated and provided by the RF tag means, 3000, as back-scatter; stray EMI/EMF signals, and, generally unavoidable internal circuit noise.

Since the resultant detected signal, 16, is of an abbreviated amplitude, and since it is composed of myriad frequency components, additional circuitry is required so as to extract the desired data signal component, as first provided by the RF tag means, 3000, from the remaining frequencies and undesired signal components.

Thus we now address the RF signal conditioning circuit, 1400-B, of the analog front-end circuit, 1400:

The resultant detected signal, 16, is applied to a first lead of circuit component and predetermined capacitor device, 1405, whose remaining and second lead is applied to a first lead of circuit component and predetermined resistor device, 1406, which the components, 1405 and 1406, together act, in part, as a first filter means, and which provide a first variant signal, noted as 16A, derived from the resultant detected signal, 16, to the inverting input of circuit component and predetermined operational amplifier device, 1429, and, a first lead of circuit component and predetermined resistor device, 1409, whose remaining and second lead, is applied to the output of the circuit component and operational amplifier device, 1429.

The circuit component and operational amplifier device, 1429, then amplifies the first variant signal 16A, according to the value relationship of circuit components and resistors 1406 and 1409, and provides an amplified version of the first variant signal, 16A, at its output as a first amplified signal, noted as signal 21.

Applied around the non-inverting input and the output of circuit component and operational amplifier device, 1429, one will note items 1419 and 1420, both: predetermined NPN transistors, configured as virtual diode limiter devices.

The predetermined use of the NPN transistors and items 1419 and 1420 is because the parameter of "distance sensing" is a substantial prerequisite and factor in the design of the present invention, and as such, common diode devices, such as: ln4148's, could not be incorporated, as they exhibit instability, high leakage and conductance, and unsuitable capacitance, even at room temperature; especially observable when applied signals to the common diode devices are approximately +/−70 or so millivolts in amplitude, or less.

The present invention allows for sensing applied signals less than 70 millivolts in amplitude, therefore common diode devices non-ideally affect desired signal integrity when amplified. To clarify, the fundamental reason for using NPN transistors and items 1419 and 1420, is to provide for a more stable signal at the first amplified signal 21 when the applied resultant detected signal 16 contains only a few millivolts of observable back-scatter and data stream signal component.

Predetermined component and capacitor device, 1425, acts to provide enhanced signal integrity and stability, and provides frequency compensation about the circuit component and operational amplifier device, 1429.

Pausing, to draw attention to predetermined items 1439, a circuit component and resistor device, 1440, a circuit component and resistor device, and, 1441, a circuit component and capacitor device, these components are utilized to obtain a predetermined voltage of 2.5 volts, by means wherein the circuit components and resistor devices, 1439, and 1440, and by virtue of their physical incorporation and intrinsic values, divide the applied circuit voltage by 2, and whereafter, circuit component and capacitor device, 1441, acts as a filter and signal stabilizer for the voltage of 2.5 volts, noted as signal 17.

To overcome certain impedance factors associated with items 1439, and 1440, the circuit components and resistor devices, and, 1441, the circuit component and capacitor device, signal 17 is applied to the non-inverting inputs of three predetermined operational amplifiers, noted as items 1438, 1437, and 1436, wherein each of which is configured as a voltage follower apparatus.

The operational amplifiers, 1438, 1437, and 1436, each have at their respective outputs, signals: 20, 19, 18, a voltage signal which is also 2.5 volts, but which each now remain of a lo-impedance nature. The signals, 20, 19, 18, are then applied to certain other predetermined operational amplifier devices (items 1431, 1430, and item 1429, respectively) as first predetermined circuit voltage reference signals C, B, and A, respectively.

Thus and to continue: Signal 18 is applied to a first lead of predetermined circuit component and resistor device, 1434. The value of circuit component and resistor device, 1434, was so chosen to approximately equal the parallel resistance value of the circuit components and resistor devices, 1406, and, 1409, so as to reduce offset errors at the operational amplifier device, 1429. The remaining and second lead of circuit component and resistor device, 1434, as signal A, a first predetermined circuit voltage reference signal, is then applied to the non-inverting input of the operational amplifier device, 1429, completing the desired circuit about the operational amplifier device, 1429.

Now, the first amplified signal, 21, outputted from the operational amplifier device, 1429, is then applied to a first lead of circuit component and predetermined resistor device, 1410, whose remaining and second lead, is applied to a first lead of circuit component and predetermined resistor device, 1412, whose remaining and second lead, is then applied to the inverting input of circuit component and predetermined operational amplifier device, 1430, and, a first lead of circuit component and predetermined resistor device, 1413, whose remaining and second lead, is applied to the output of the circuit component and operational amplifier device, 1430.

However, the circuit component and resistor device, 1411, has attached across it, a circuit component and predetermined capacitor device, 1411, which, in synchronicity with the circuit components and resistor devices, 1410, and 1412, form a second filter means.

In addition, the raw input signal, 15, provided by both: the cathode of the diode and item 1401, and anode of the diode and item 1402, is, as shared above, applied to a first lead of circuit component and predetermined capacitor device, 1407, whose remaining and second lead is then applied to a first lead of circuit component and predetermined resistor device, 1408, which together act, as a third filter means. The remaining and second lead of the circuit component and resistor device, 1408, provides for a first alternate signal of the applied output signal 2, noted as 15A, to the inverting input of the circuit component and operational amplifier device, 1430.

The additive combination of the independent signals, as provided by: the second lead of circuit component and resistor device, 1408, i.e., signal 15A, and, the second leads of paralleled circuit components, 1412 and 1411, together, provide for a second variant signal, 21A.

The circuit component and operational amplifier device, 1430, then amplifies the second variant signal, 21A, according to the value relationship of circuit components and resistors 1410, 1412, and 1413, and provides an amplified version of the second variant signal, 21A, at its output as a second amplified signal, noted as signal 22.

Applied around the inverting input and the output of circuit component and operational amplifier device, 1430, one will note items 1421 and 1422, both: predetermined NPN transistors, configured as virtual diode limiter devices. Referring back to the transistors and items 1419 and 1420, and the discussion thereof, the reason for the use of the NPN transistors and items 1421 and 1422, remains essentially the same as that for using the NPN transistors and items 1419 and 1420, and as such, need not be recounted.

Circuit component and predetermined capacitor device, 1426, acts to provide enhanced signal integrity and stability, and provides frequency compensation about the circuit component and operational amplifier device, 1430.

The voltage reference signal, 19, is applied to a first lead of circuit component and predetermined resistor device, 1435. The value of circuit component and resistor device, 1435, was so chosen to approximately equal the parallel resistance value of the circuit components and resistor devices, 1410, 1412 and 1413, so as to reduce offset errors at the operational amplifier device, 1430. The remaining and second lead of circuit component and resistor device, 1435, as signal B, first the predetermined circuit voltage reference signal is then applied to the non-inverting input of the operational amplifier device, 1430, completing the desired circuit about the operational amplifier device, 1430.

Now, the second amplified signal, 22, outputted from the operational amplifier device, 1430, is then applied to a first lead of circuit component and predetermined capacitor device, 1414, whose remaining and second lead is applied to a first lead of circuit component and predetermined resistor device, 1415, which the components, 1414 and 1415, together act, in part, as a fourth filter means, and which provide a third variant signal, noted as 22A, derived from the amplified signal, 22, to the inverting input of circuit component and predetermined operational amplifier device, 1431, and, a first lead of circuit component and predetermined resistor device, 1416, whose remaining and second lead, is applied to the output of the circuit component and operational amplifier device, 1431.

The circuit component and operational amplifier device, 1431, then amplifies the third variant signal, 22A, according to the value relationship of circuit components and resistors 1415 and 1416, and presents an amplified version of the third variant signal, 22A, at its output as a third amplified signal, noted as signal 25.

Applied around the inverting input and the output of circuit component and operational amplifier device, 1431, one will note items 1423 and 1424, both predetermined NPN transistors, configured as virtual diode limiter devices. Referring back to the transistors and items 1419 and 1420, and the discussion thereof, the reason for the use of the NPN transistors and items 1423 and 1424, again remains essentially the same as that for using the NPN transistors and items 1419 and 1420, and as such, need not be repeated.

Circuit component and predetermined capacitor device, 1427, acts to provide enhanced signal integrity and stability, and provides frequency compensation about the circuit component and operational amplifier device, 1431.

The voltage reference signal, 20, is applied to a first lead of circuit component and predetermined resistor device, 1433. The value of circuit component and resistor device, 1433, was so chosen to approximately equal the parallel resistance value of the circuit components and resistor devices, 1415 and 1416, so as to reduce offset errors at the operational amplifier device, 1431. The remaining and second lead of circuit component and resistor device, 1433, as signal C, a first predetermined circuit voltage reference signal, is then applied to the non-inverting input of the operational amplifier device, 1431, completing the desired circuit about the operational amplifier device, 1431.

Now, the third amplified signal, 25, outputted from the operational amplifier device, 1431, is then applied to a first lead of circuit component and predetermined resistor device, 1417, whose remaining and second lead, providing for a fourth variant signal, noted as 25A, derived from the amplified signal, 25, is applied to the inverting input of circuit component and predetermined operational amplifier device, 1432, and, a first lead of circuit component and predetermined resistor device, 1418, whose remaining and second lead, is applied to the output of the circuit component and operational amplifier device, 1432.

The circuit component and operational amplifier device, 1432, then amplifies the fourth variant signal, 25A, according to the value relationship of circuit components and resistors 1417 and 1418, and presents an amplified version of the variant signal, 25A, at its output as a fourth amplified signal, noted by nomenclature: "DATA" and as signal 26, and, a subsequent and fifth amplified signal, noted as signal 27, a final circuit signal.

Pausing, to draw attention to circuit component and predetermined resistor device, 1442, and circuit component and predetermined resistor device, 1443, these components are utilized to obtain a predetermined reference voltage of 2.7 volts, by means wherein the circuit components and resistor devices, 1442, and 1443, and by virtue of their physical incorporation and intrinsic values, predeterminedly divide the applied circuit voltage, and whereafter, circuit component and predetermined capacitor device, 1444, acts as a filter and signal stabilizer for the predetermined reference voltage of 2.7 volts, noted now as signal 23.

To overcome certain impedance factors associated with the items 1442, and 1443, the circuit components and resistor devices, and, 1444, the circuit component and capacitor device, signal 23 is applied to the non-inverting input of predetermined operational amplifier, noted as item 1445, wherein the item 1445 is configured as a voltage follower apparatus, which provides at its output, signal 24, a second predetermined voltage reference signal.

Thus and to continue: Signal 24 is applied to a first lead of circuit component and predetermined resistor device, 1428. The value of circuit component and resistor device, 1428, was so chosen to approximately equal the parallel resistance value of the circuit components and resistor devices, 1417, and, 1418, so as to reduce offset errors at the operational amplifier device, 1432. The remaining and second lead of circuit component and resistor device, 1432, as signal D, the second predetermined circuit voltage reference signal, is then applied to the non-inverting input of the operational amplifier device, 1432, completing the desired circuit about the operational amplifier device, 1432.

The subsequent and fifth amplified signal, noted as final circuit signal, 27, is ultimately applied to predetermined input and pin D of the microcontroller device means, 1100-A, of FIG. 2, allowing for receiving the final circuit signal, 27 by the microcontroller device means, 1100-A.

Figure 7:
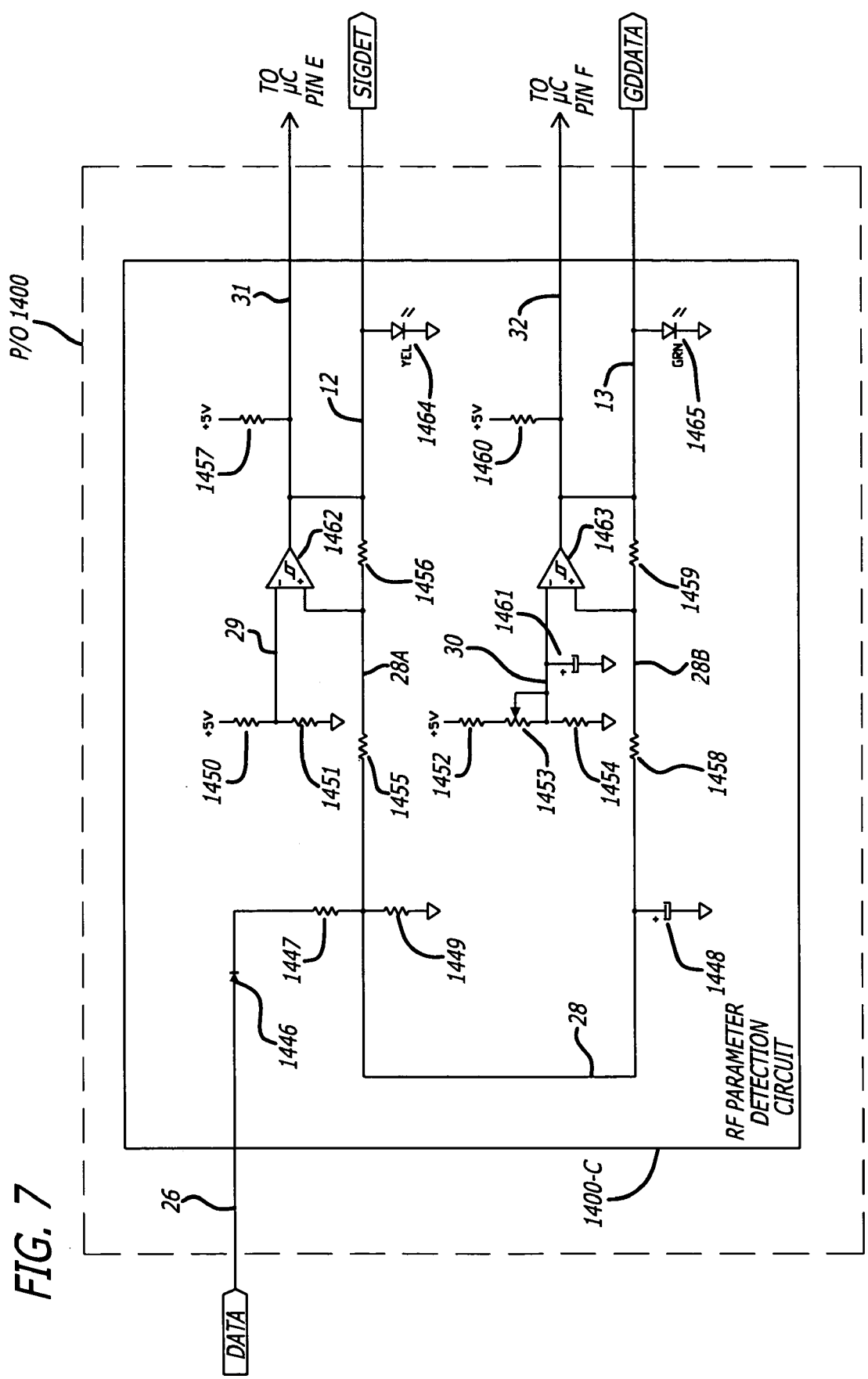
FIG. 7 depicts a portion of a schematic diagram of an embodiment of the RFID transducer alignment system according to the present invention.

The fourth amplified signal, noted by nomenclature: "DATA" and as signal 26, is ultimately applied to the anode of predetermined circuit component and diode device, noted as item 1446 of the remaining portion and second partial drawing of the analog front-end, 1400, which we now review:

Referring to FIG. 7 now, the fourth amplified signal, noted by nomenclature: "DATA" and as signal 26, is applied to the anode of the diode device, 1446, of the remaining portion of the analog front-end, 1400, which comprises an RF parameter detection circuit.

The cathode of the circuit component and diode, 1446, a rectifier, is made to couple to a first lead of predetermined circuit component and resistor, item 1447, whose second and remaining lead is then coupled to a first lead of predetermined circuit component and resistor, 1449, and, predetermined circuit component and capacitor, 1448, where together, these the components provide means allowing for a third predetermined circuit voltage reference signal to be created, noted as signal 28.

The value of the predetermined circuit component and resistor, 1447, is chosen to establish a minimum voltage base level from which certain predetermined parameters of the final circuit signal, 26, may ultimately be detected, and may be construed to be predicated on the partial or whole data content of the final circuit signal, 26, wherein the data content is comprised of logically: HI and LO appearing waveforms. The waveforms, when integrated, by additional means of circuit component and capacitor, 1448, provide a predetermined D.C. voltage level to the inputs and first leads of predetermined circuit components and resistors, 1455, and, 1458.

Now then, predetermined circuit component and resistor, item 1450, has a first lead attached to the applied circuit voltage, for example, +5V, and has a second and remaining lead attached to a first lead of predetermined circuit component and resistor, item 1451, whereby together, items 1450 and 1451 provides means allowing the creation of a fourth predetermined circuit voltage reference signal, noted as signal 29, which is then applied to the inverting input of predetermined comparator device, 1462.

The first lead of the circuit component and resistor, 1455, receiving the third circuit voltage reference signal, 28, has attached to its second and remaining lead, a first lead of predetermined circuit component and resistor, 1456, providing for a fifth predetermined circuit voltage reference signal, noted as signal 28A, and, wherein the remaining and second lead of the resistor and item 1456 is then applied to the output of the comparator device, 1462.

The values of the circuit components and resistors, 1455, and, 1456, are so chosen as to establish both: a predetermined impedance, and, a predetermined hysteresis about the comparator device, 1462, wherein also, the fifth circuit voltage reference signal, 28A, is presented to the non-inverting input of the comparator device, 1462.

As is well understood by those skilled in the art, a common voltage comparator device acts to differentiate between two independently applied input signals, i.e.: the given signals presented to both: the inverting AND non-inverting inputs of the common voltage comparator device, whereby the output of which, will predeterminedly switch from a logical HI state, to a logical LO state, or vice versa, predicated on the voltage potentials of the applied input signals.

The comparator device, 1462, will switch its output logically LO when the fifth circuit voltage reference signal, 28A, is less than the fourth circuit voltage reference signal, 29, causing predetermined circuit component and LED device, 1464, to remain dark, thereby indicating no given RF tag device has been detected, and providing, by means of signal 12, noted by nomenclature: "SIGDET", a first predetermined RF parameter detection signal, indication of the same to the RF reader circuit, 2000, and ultimately, to the RF transponder means, 1000.

Contrarily, the comparator device, 1462, will switch its output logically HI when the fifth circuit voltage reference signal, 28A, is greater than the fourth circuit voltage reference signal, 29, by means of the circuit component and resistor, 1457, thereby causing illumination of the circuit component and LED device, 1464, indicating a given RF tag device has been detected, and providing, again by means of the signal 12, "SIGDET", the first predetermined RF parameter detection signal, indication of the same to the RF reader circuit, 2000, and ultimately, to the RF transponder means, 1000.

The output of the comparator device, 1462, additionally provides for a subsequent output signal, 31, ultimately presented to predetermined input and pin E of the microcontroller device means, 1100-A, of FIG. 2, allowing for receiving the first predetermined RF parameter detection signal, 31, by the microcontroller device means, 1100-A.

Finally, predetermined circuit component and resistor, item 1452, has a first lead attached to the applied circuit voltage, for example, +5V, and has a second and remaining lead attached to a first lead of predetermined circuit component and resistor, item 1453, whose second and third remaining leads are then attached to a first lead of predetermined circuit component and resistor, item 1454, the junction of which, is connected to the first lead of a predetermined circuit component and capacitor, item 1461, whereby together, the items 1452-1454 and 1461 provide means allowing the creation of a sixth predetermined circuit voltage reference signal, noted as signal 30, which is then applied to the inverting input of predetermined comparator device, 1463.

It ought be noted: predetermined circuit component and resistor, item 1453, is variable, and provides means for obtaining a 2 to 3 volt sixth predetermined circuit voltage reference signal, noted as signal 30, and, can also be of a programmable type, controlled by a microcontroller device if needed or desired.

To continue: The first lead of the circuit component and resistor, 1458, receiving the third circuit voltage reference signal, 28, has attached to its second and remaining lead, a first lead of predetermined circuit component and resistor, 1459, providing for a seventh predetermined circuit voltage reference signal, noted as signal 28B, and, wherein the remaining and second lead of the resistor and item 1459 is then applied to the output of the comparator device, 1463.

The values of the circuit components and resistors, 1458, and, 1459, are so chosen as to establish both: a predetermined impedance, and, a predetermined hysteresis about the comparator device, 1463, wherein also, the seventh circuit voltage reference signal, 28B, is presented to the non-inverting input of the comparator device, 1463.

The comparator device, 1463, will switch its output logically LO when the seventh circuit voltage reference signal, 28B, is less than the sixth circuit voltage reference signal, 30, causing predetermined circuit component and LED device, 1465, to remain dark, thereby indicating no valid data stream signal has been detected, and providing, by means of signal 13, noted by nomenclature: "GDDATA", a second predetermined RF parameter detection signal, indication of the same to the RF reader circuit, 2000, and ultimately, to the RF transponder means, 1000.

Contrarily, the comparator device, 1463, will switch its output logically HI when the seventh circuit voltage reference signal, 28B, is greater than the sixth circuit voltage reference signal, 30, by means of the circuit component and resistor, 1460, thereby causing illumination of the circuit component and LED device, 1465, indicating a valid data stream signal has been detected, and providing, again by means of the signal 13, "GDDATA", the second predetermined RF parameter detection signal, indication of the same to the RF reader circuit, 2000, and ultimately, to the RF transponder means, 1000.

The output of the comparator device, 1463, additionally provides for a subsequent output signal, 32, ultimately presented to predetermined input and pin F of the microcontroller device means, 1100-A, of FIG. 2, allowing for receiving the second predetermined RF parameter detection signal, 32, by the microcontroller device means, 1100-A.

It remains yet other predetermined RF parameter detection signals can be obtained, if desired, such as the parameter of distance, within limits, and as concerns: a given RF tag device to a given RF transponder/RF reader device, by means of additional circuitry and associative circuit signals.

Now that the new and inventive RFID transponder alignment system, providing for broadened operational functionality, and altogether new RFID applications, has been specifically described, it remains that certain aspects of the design can, or may be alternatively modified from the preferred embodiment, and, in lieu of the foregoing, will momentarily be described in appurtenant detail. However, it is to be understood the following alternate embodiments are given by way of example only, and are not intended to suggests limits, of any nature, to the scope and/or spirit of the present invention, or as regards application.

As to alternative embodiments, it is assumed the reviewer now has a good understanding of the construction, function, and benefits of the above addressed embodiment of the present invention. In discussing the following alternate embodiments then, the focus will remain on implementation and/or application of the alternate embodiments.

Figure 8:
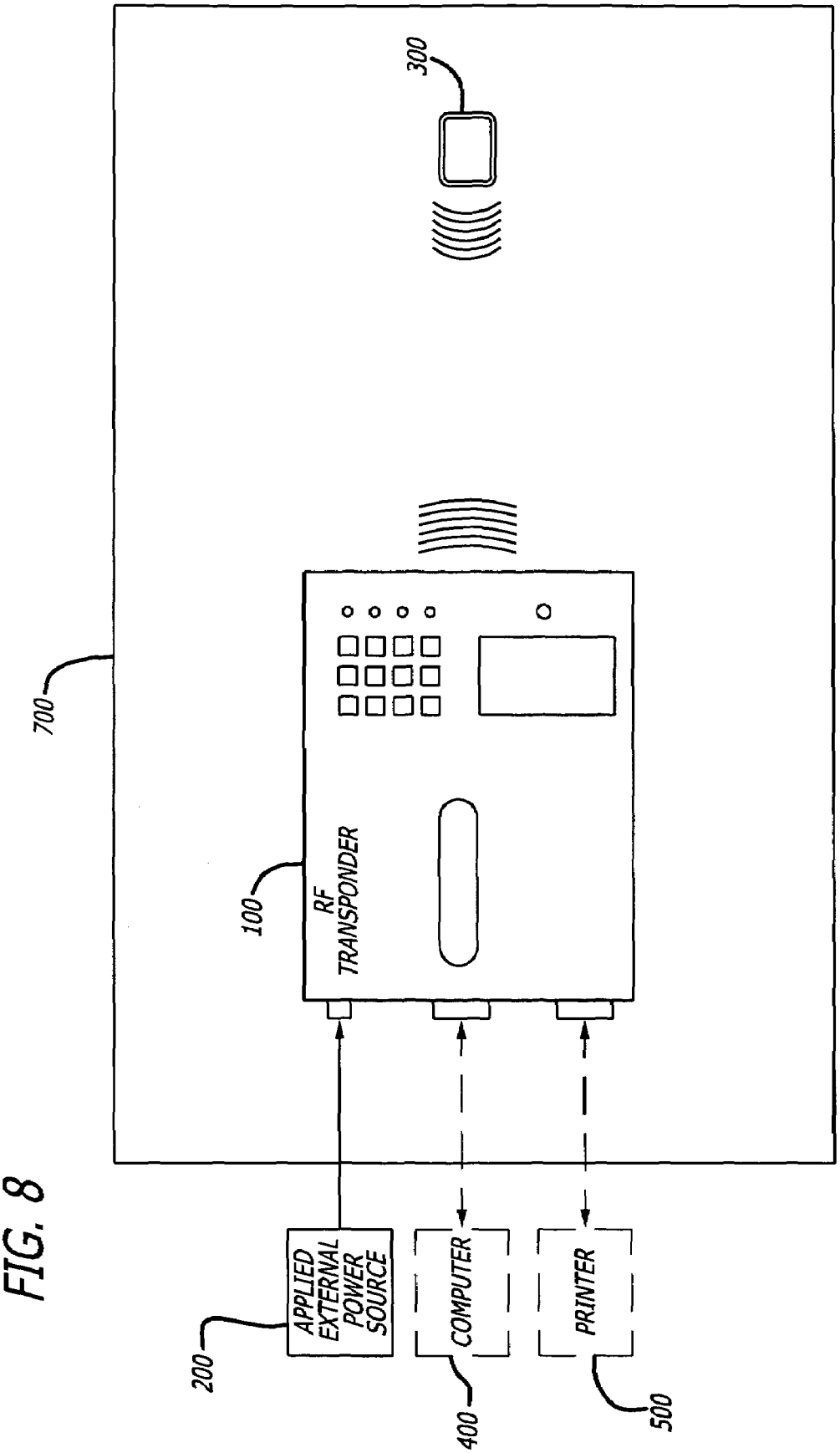
FIG. 8 is a schematic representation of an alternate embodiment of an RF transducer alignment system of the present invention illustrating an example of a hand-held apparatus having both an RF transponder and an RF reader.

To begin with, FIG. 8 depicts an example embodiment and application of the present invention, 700, wherein a hand-held RF transponder means, 100, is illustrated. The merit of items 200, 400, and 500 have already been addressed with regard to FIG. 1, items: 5000, 6000, and 7000, respectively, and need not be re-elaborated on here.

However, item 100 of FIG. 8 represents a top-view of a self-contained RF transponder system apparatus, wherein it is composed of an RF transponder means, and, an RF reader means. As a small enclosed, light weight package, it intrinsically offers many benefits, both: to end-users, and, as regards portable or mobile applications.

Figure 9:
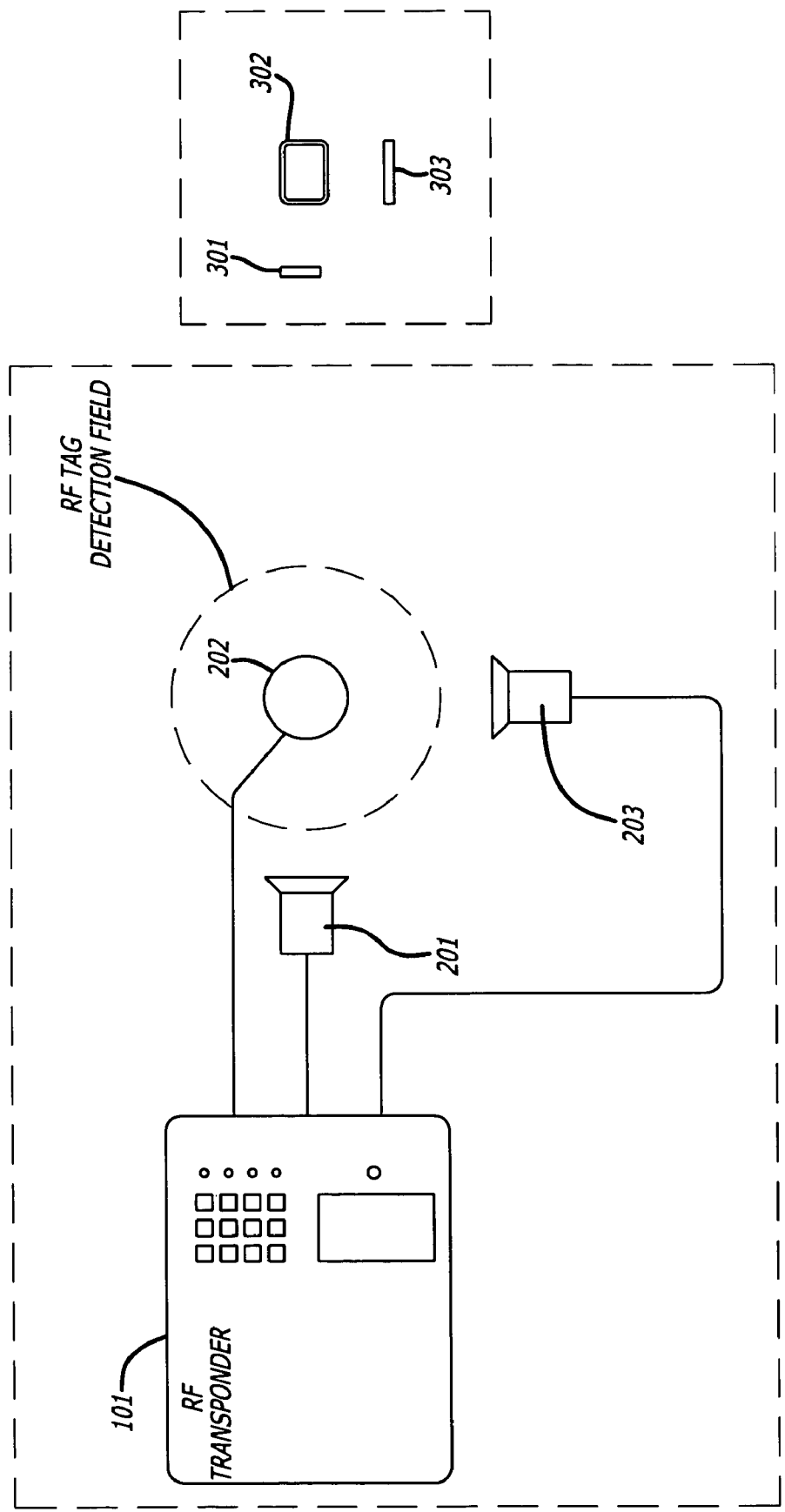
FIG. 9 is a schematic representation of an alternate embodiment of an RF transducer alignment system of the present invention illustrating a multi-axis alignment system having three RF readers and three RF tags in an "x", "y", and "z" orientation.

FIG. 9 depicts an example embodiment and application of the present invention, wherein an application requiring the use of "x", "y", and "z" coordinates is illustrated, for say: medical instrumentation, and/or where: diagnosis and/or treatment procedures and/or equipment is concerned.

If item 101, an integrated RF transponder means, is attached to a computerized (at some level) medical apparatus, the RF transponder means, 101, can, at a minimum, provide certain information about the location and critical alignment of items: 301-303, certain RF tag means, arranged in "x", "y", and "z" coordinates, by means of items: 201-203, remote RF reader means, also arranged in "x", "y", and "z" coordinates, wherein the RF reader, 201, is responsive only to the RF tag, 301, and vise versa; and, wherein the RF reader, 202, is responsive only to the RF tag, 302, and vise versa; and wherein the RF reader, 203, is responsive only to the RF tag, 303, and vise versa, providing for an enhanced RF transducer alignment system.

Such a system could be attached to, or about, say: a (perhaps semi-automated) radiation device and apparatus for say: cancer treatment. Variant embodiment RF tags placed on a given patient's body, or, about the body, could allow, at a minimum, for precise alignment of the radiation device and apparatus, so as to eventually execute a reliably placed radiation treatment.

Additionally, RF readers, 201-203, could be fabricated such that each RF reader is positionally adjustable as to its assigned/dominant axis, providing for instances wherein the "x", "y", and "z" RF tags might be positioned in obtuse ways to each other, and therefore, the RF tags might not necessarily be positioned in a geometrically equal way about each other, and in fact, may reside at unequal distances and/or positions from each other.

Additionally still, RF readers, 201-203, could be fabricated such that each, or all the RF readers are adjustable about a given, or expected, RF tag detection field (see: FIG. 9, upper middle nomenclature and dashed circle), wherein "standard convention" geometric: "x", "y", and "z" coordinates might not be practical, and thus the RF readers might accommodate being widely repositionable about three-dimensional space.

Figure 10:
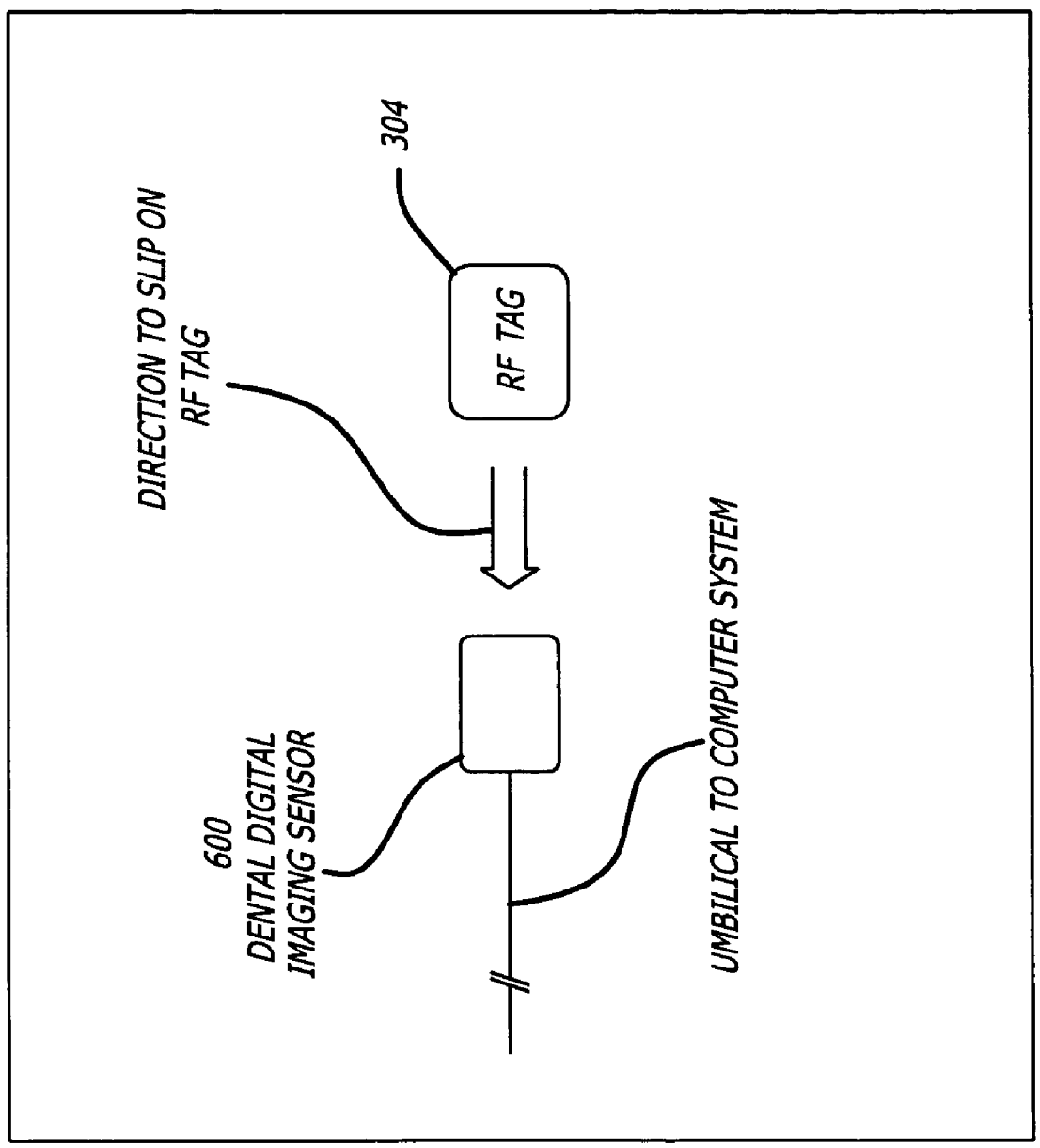
FIG. 10 is a schematic representation of an alternate embodiment of an RF transducer alignment system of the present invention illustrating a dental digital x-ray imaging sensor and an RF tag device.

FIG. 10 depicts an example embodiment and application of the present invention, wherein digital radiography is utilized, and specifically illustrated, is a side-view of a dental digital imaging sensor, 600, wherein also is illustrated, a slip-on RF tag means, 304. The RF tag, 304, a (perhaps reusable) device, would slip over the digital imaging sensor, 600, 50 that, and utilizing the present invention, one may obtain exacting x-ray images, by means provided by the RF tag means, 304, and the present invention.

FIG. 11 depicts an example embodiment and application of the present invention, wherein a portable RF transponder apparatus, 703, is shown constructed, looking similar in nature to a given field-applicable metal detector device, wherein item 701 provides for a handle, and wherein item 702, a modified and remote RF reader means, labeled: "multi-form reader coil", provides for RF tag detection, by means of two predeterminedly sized carrier transmit/data receive coils, each possibly operating at differing frequencies, and possibly, at differing power levels, by means of predetermined RF waveform drive signals: DRIVE 1, and DRIVE 2, and wherein, each RF reader coil might be able to be predeterminedly used, independently from the other, and/or, in synchronicity with each other.

To illustrate by example, one implementation: Item 702-A, the larger of the carrier transmit/data receive coils, might generally provide for broad-field RF tag detection only, wherein item 702-B, the smaller of the carrier transmit/data receive coils, might generally provide for near-field RF tag detection, as well as critical alignment RF tag detection.

Figure 12A:
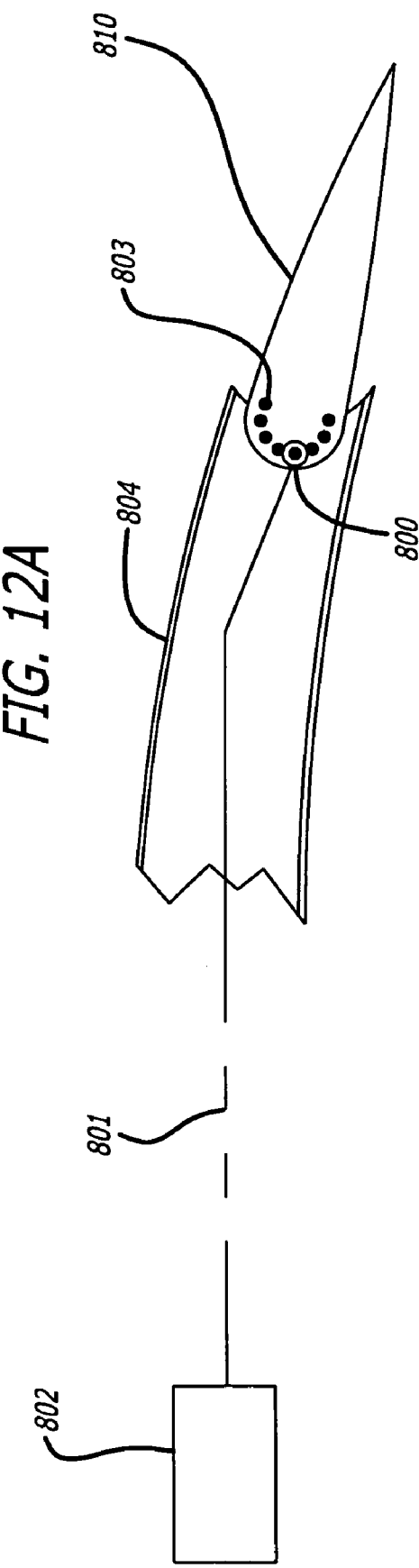
FIGS. 12A & 12B are schematic representations of an alternate embodiment of an RF transducer alignment system of the present invention illustrating a multi-point RF tag detection and alignment feedback system for a winged aircraft.
Figure 12B:
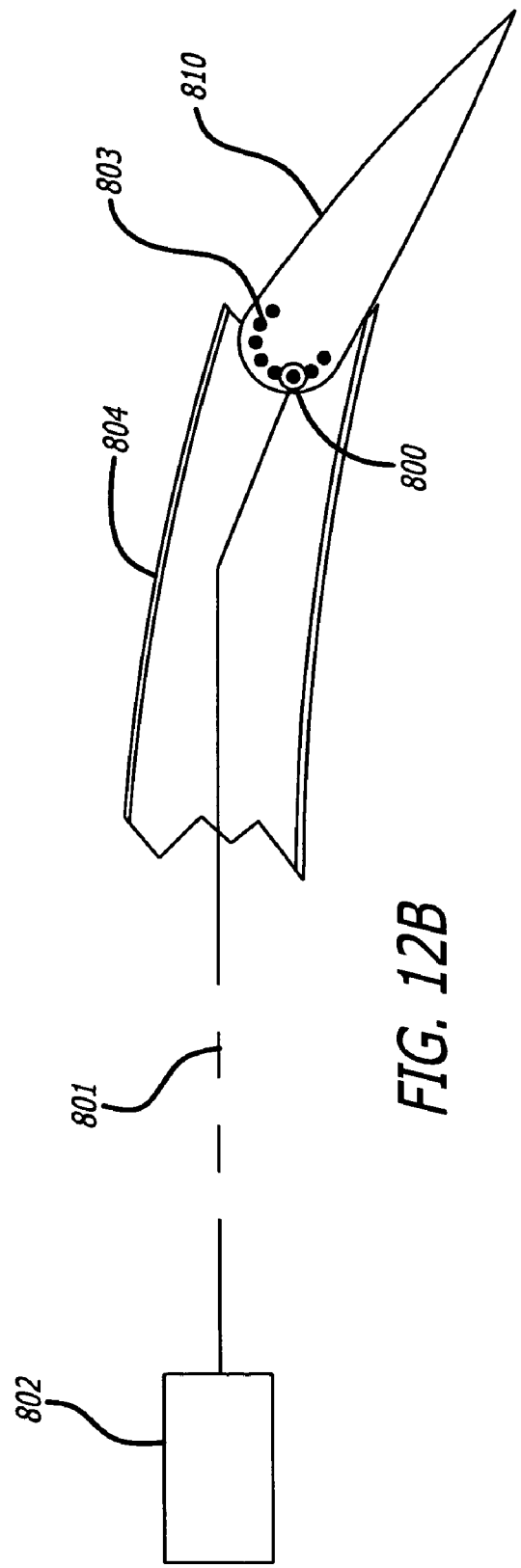

FIG. 12 depicts an example embodiment and application of the present invention, wherein a multi-RF tag arrangement, via items 803, is utilized with an RF reader means, 800, so as to identify exacting attitude of an alterable-position flight-surface of an airfoil 804, wherein item 810, the alterable-position flight-surface of the top-most figure, FIG. 12A, depicts a "level flight" position and attitude, and wherein item 810, also the alterable-position flight-surface, but illustrated in the bottom-most figure, FIG. 12B, depicts a "dive/descend" position and attitude.

Item 801, an umbilical cable provides certain predetermined signals to and from item 802, a given flight surface control computer, which has the built-in capability to critically identify the position of all flight surfaces on/of a given aircraft. Since the RF tags need not protrude from the flight surfaces, and since they are not prone to wear, contamination, or rust, etc., and, need no outside attached power source, they, with an alternate embodiment of the present invention, configured to interface with the flight surface control computer, 802, provide an ideal platform whereby a pilot, and/or certain nav-computers, can critically monitor all movable flight surfaces, and potentially, by means of the nav-computers software, provide "safing" measures when "expected" or "normal", etc. RF tag signals fail to manifest from the RF reader devices, 800.

Figure 13:
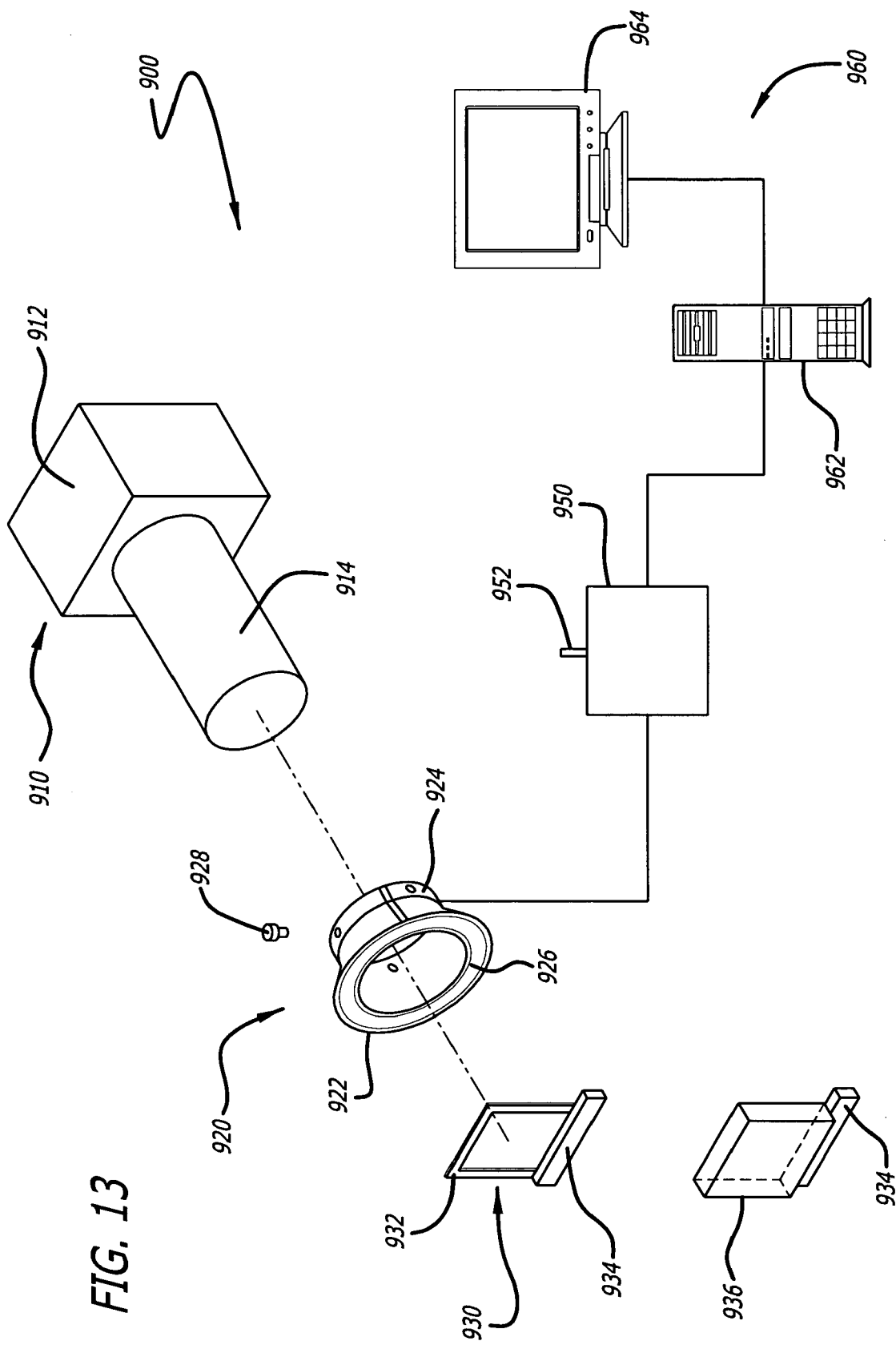
FIG. 13 is a schematic representation of the RFID alignment system of the present invention applied to a dental x-ray apparatus.

Referring now to FIG. 13, an example RFID alignment system, 900, of the present invention, does not include, but may be applied to a dental x-ray apparatus 910, having an x-ray emitter, 912, and extension tube, 914. An RF reader assembly, 920, is configured to be removably or fixedly installed on the extension tube of the x-ray apparatus. The RF reader assembly includes a hollow cylindrical portion, 924, configured to concentrically slide onto, or otherwise attach to the x-ray extension tube. The portion of the RF reader assembly that attaches to the extension tube may be configured with an attachment device, such as screws, 928, for fixing the RF reader assembly to the x-ray tube. The RF reader assembly may further include a flange, 922, or may be otherwise configured to contain at least one coil, 926. Seating the coil(s) in the holder should be precise and concentric so as to establish proper alignment between the x-ray emitter and an x-ray sensitive film or sensor coupled to an RF tag. The coil(s) may be glued into the flange or seat of the RF reader assembly and a face plate may be provided so that the coil(s) is/are not exposed to the environment.

Channels may be provided within the RF reader assembly to house the wires from the coil(s), which ultimately attach to a RF transponder assembly, 950. An indicator, 952, such as an LED or other lamp device, may be mounted at or near the RF transponder assembly, 950, to ultimately indicate an achieved alignment condition. The RF transponder assembly may be operably connected to a computer system, 960. Such a computer system may include a microprocessor-based tower, 962, and a display device, 964. The computer system may be used to further process signals as presented from the RF transponder and store associated patient information.

The dental x-ray system further includes an imaging device, 930, having a frame, 932, which provides for inserting an x-ray sensitive film and for embedding an RF tag, and which is made to be integral to an x-ray film holder assembly (bitewing), 934. Alternatively, the imaging device, 930, may be constructed to have a frame, 936, which provides for inserting an x-ray sensitive digital sensor in synchronicity with a digital sensor bitewing, 934. The RF tag may be programmed to contain patient information, such as social security number, invoice number, time, date, tooth location, and other dental records. The RF tag coil(s) may be configured in frame, 932, 50 that it/they will not cover the surface of the film or sensor and may lay coplanar around the film (or sensor) in a circular or rectangular shape, leaving the surface of the film or sensor clear for the image. Alternatively, the RF tag may be constructed so as to be placed directly into or about an x-ray sensitive film, or into or about an x-ray sensitive digital sensor. A software package may be provided for the external computer system, 960, that communicates through standard data communication protocols to the RF transponder assembly, 950.

In operation, the RF reader assembly, 920, may be installed on the extension tube, 914, of the x-ray apparatus, 910. The film holder assembly, 930, is inserted into the patient's mouth and the x-ray operator enables the RF transponder, 950. When the RF reader assembly, 920, and the RF tag assembly, 930, are, as an example, aligned parallel and concentric, an indicator light, 952, may show that the system is critically aligned and the radiograph is ready to be taken. Alternatively, the RF transponder may be configured such that it may inhibit powering of the x-ray emitter until such critical alignment occurs.

Thus and in conclusion, there has been demonstrated a versatile, inventive, economical, and beneficial RFID transponder alignment system, providing for broadened operational functionality, and altogether new RFID applications, independent of any given embodiment. With such a beneficial and suitable design, with manifold applications with which to apply the present invention, wide use could not only result in a great deal of user-satisfaction and benefit, as well as improved manufacturers end-product(s), but in some instances, result in certain financial savings for the end-user, or others.

While a particular form of the present invention has been illustrated and described, it will be apparent to those skilled in the art that various modifications can be made without departing from the inventive concept. Accordingly, it will be understood by those skilled in the art that certain changes in function, form, capacity, size, shape, and/or other detail may be made without departing or detracting from the spirit and scope of the present invention. Accordingly, it is not intended that the invention be limited except by the appended claims.

We claim:

1. A radio frequency alignment system, comprising:
   a radio frequency transponder configured to control a first electromagnetic flux field, and further configured to detect and process received emissions containing alignment parameters from a second electromagnetic flux field within a predetermined area of alignment;
   a radio frequency tag configured to emit the second electromagnetic flux field in response to the first electromagnetic flux field; and
   a radio frequency reader configured to emit a first electromagnetic flux field, and further configured to receive the second electromagnetic flux field.

2. The system of claim 1, wherein the radio frequency transponder further includes a user interface and is further configured to activate an indicator when the transponder detects the alignment parameters from the second electromagnetic flux field from the radio frequency tag.

3. A radio frequency alignment system, comprising:
   at least one RF transponder, configured in part to provide for one or more RF readers, and further configured to provide for predefined sensing of, predefined processing of, predefined indication of, and predefined response to, a plurality of predetermined RF transducer system alignment parameters relative to one or more predefined radio frequencies and at least two predefined electromagnetic flux fields, as specifically regards the relative placement or positioning of an RF reader to an RF tag, or vise versa, in predefined three dimensional space;
   one or more predefined RF readers, each constructed with one or more coil devices and predeterminedly configured to provide for operation at one or more predefined radio frequencies, the predetermined emitting of a plurality of first electromagnetic flux fields, and the predetermined receiving of a plurality of second electromagnetic flux fields, providing, in part, for the ability of a preconfigured RF transducer system to denote a multiplicity of ascribed alignment parameters; and
   at least one RF tag, constructed with one or more coil devices and predeterminedly configured to provide for operation at one or more predefined radio frequencies, the predetermined receiving of a plurality of first electromagnetic flux fields, and the predetermined emitting of a plurality of second electromagnetic flux fields in response to the presence of one or more first electromagnetic flux fields, providing, in part, for the ability of a preconfigured RF transducer system to denote a multiplicity of ascribed alignment parameters.

4. The system of claim 3, wherein an RF transponder is further configured to comprise:
   means providing for selective control of an RF reader, whereby emissions of a first predetermined electromagnetic flux field may ultimately be generated with respect to ascribed RF transducer system alignment parameters; and
   means providing for predefined detection and selective processing of emissions of a second predetermined electromagnetic flux field ultimately received by an RF reader with respect to ascribed RF transducer system alignment parameters.

5. The system of claim 3, wherein an RF reader is further configured to comprise:
   means providing for emitting a plurality of first predetermined electromagnetic flux fields, with respect to ascribed RF transducer system alignment parameters; and
   means providing for receiving a plurality of second predetermined electromagnetic flux fields, with respect to ascribed RF transducer system alignment parameters.

6. The system of claim 3, wherein an RF tag is further configured to comprise:
   means providing for the selective receiving and processing of at least one first predetermined electromagnetic flux field, with respect to ascribed RF transducer system alignment parameters;
   means providing for selective responses to at least one first predetermined electromagnetic flux field, with respect to ascribed RF transducer system alignment parameters; and
   means providing for the selective emitting of at least one second predetermined electromagnetic flux field, with respect to ascribed RF transducer system alignment parameters.

7. The system of claim 3, wherein an RF transponder is further configured to comprise:
   means providing for a user interface having attributes which are selectable and programmable, and which contains at least one indicator device, providing thereby for intimate system control and operation; and
   means providing for a plurality of predefined system features and functions, and for providing for predefined indication of at least one predefined system feature or function, with respect to ascribed RF transducer system alignment parameters; and
   means providing for a plurality of predefined system responses, and for providing for predefined indication of at least one predefined system response, with respect to ascribed RF transducer system alignment parameters; and
   means providing for interfacing with external devices or apparatus, as examples, a printer, a computer, an x-ray machine, and/or other electronic or medical devices or apparatus.

8. The system of claim 3, wherein an RF reader is further configured to comprise:
   means providing for indication of at least one predefined system function, with respect to ascribed RF transducer system alignment parameters; and
   means providing for indication of at least one predefined system response, with respect to ascribed RF transducer system alignment parameters.

9. The system of claim 3, wherein an RF transponder and an RF reader in synchronicity are together configured with respect to ascribed RF transducer system alignment parameters, whereby:
   at least one first predetermined electromagnetic flux field is ultimately emitted;
   at least one second predetermined electromagnetic flux field provided by an RF tag is ultimately received; and
   predetermined alignment criterion with regard to the proximal arrangement of an RF reader to an RF tag, or vise versa, may ultimately be determined.

10. The system of claim 3, wherein an RF reader and an RF tag in synchronicity are together configured with respect to ascribed RF transducer system alignment parameters, whereby:
   an RF reader acts to provide at least one first predetermined electromagnetic flux field;

circuitries within an RF tag responsive to at least one first predetermined electromagnetic flux field may become excited;

upon circuitries within an RF tag becoming excited, an RF tag acts to emit at least one second predetermined electromagnetic flux field;

an RF reader additionally acts to receive at least one second predetermined electromagnetic flux field; and received second predetermined electromagnetic flux field, in part, provides for obtaining RF transducer system alignment criterion.

11. The system of claim 3, wherein an RF reader is further configured with respect to ascribed RF transducer system alignment parameters, to attach to an x-ray emitting machine or other imaging apparatus.

12. The system of claim 3, wherein an RF tag is further configured with respect to ascribed RF transducer system alignment parameters, to attach to an x-ray sensitive imaging film or apparatus.

13. The system of claim 3, wherein an RF tag, when excited by a first predetermined electromagnetic flux field, is further configured with respect to ascribed RF transducer system alignment parameters, to utilize predefined digital data stored within its circuitries, and in at least one predefined manner, whereby:

a plurality of predefined digital data might ultimately be applied to associated RF tag circuitries to predeterminedly modulate a second electromagnetic flux field emitted by an RF tag;

the nature and extent of predefined digital data ultimately applied to modulate the emitted second electromagnetic flux field of an RF tag may be predicated, in part, on examination by an RF tag of the magnitude of a received first predetermined electromagnetic flux field, the result of which might indicate relative RF reader proximity to an RF tag, whereby there may be provided active feedback to an RF transponder as to whether or not an RF reader is within a predetermined desired operating distance to an RF tag, providing also a form of discerning insurance that predefined digital data, particularly if deemed strategic, may not be applied by an RF tag until a received first predetermined electromagnetic flux field is of an acceptable magnitude, further providing for a determination by an RF tag as to if, when, and/or what stored predefined digital data should be initially or subsequently applied to modulate the second electromagnetic flux field emitted by an RF tag; and the nature and extent of predefined digital data ultimately applied to modulate the emitted second electromagnetic flux field of an RF tag may be predicated, in part, on examination by an RF tag of the frequency of a received first predetermined electromagnetic field, the result of which might determine if an RF tag should provide a response to a proximally placed RF reader, and what that response might be, if any, providing also a form of discerning insurance that predefined digital data, particularly if deemed confidential or strategic, may not be applied by an RF tag until a received first predetermined electromagnetic flux field is of an acceptable frequency, further providing for a determination by an RF tag as to if, when, and/or what stored predefined digital data should be initially or subsequently applied to modulate the second electromagnetic flux field emitted by an RF tag.

14. The system of claim 3, wherein an RF reader is further configured with respect to ascribed RF transducer system alignment parameters, with an electronic assembly, variably comprised of:

one or more coil devices of a predetermined inductance, shape, and size; and at least one predetermined indicator device.

15. The system of claim 3, wherein an RF tag is further configured with respect to ascribed RF transducer system alignment parameters, with at least one LC tank circuit, comprised of:

at least one coil device of a predetermined inductance, shape, and size; and at least one capacitor device of a predetermined value, temperature coefficient, capacitive tolerance, and size.

16. The system of claim 3, wherein an RF tag is yet further configured with respect to ascribed RF transducer system alignment parameters, with an electronic assembly, variably comprised of:

at least one LC tank circuit responsive to at least one received first predetermined electromagnetic flux field, providing for eventual resonant excitement of said LC tank circuit and the emissions of a second predetermined electromagnetic field;

a receiving and conditioning circuit, responsive to the eventual resonating of an LC tank circuit, providing for an on-board RF tag power supply and the energizing of predefined circuitries associated with an RF tag, and providing for at least two additional signals reflective of the magnitude and frequency of at least one received first predetermined electromagnetic flux field; and a microcontroller or similar device, having a permanent yet programmable memory array capable of storing a plurality of digital data, and being capable of retaining and executing at least one predetermined program or effecting at least one predetermined set of logical steps emulating a program as provided for by said digital data, and having I/O (input/output) pins or connections, whereby a microcontroller in combination with internal or additional circuitries responsive to at least one predefined signal level reflective of the magnitude and/or responsive to at least one predefined signal level reflective of the frequency of a received first predetermined electromagnetic flux field eventually provide for retrieving and applying predefined portions of said digital data to a signal dampening circuit attached about the LC tank circuit, therewith to predeterminedly modulate the LC tank circuit and the second predetermined electromagnetic flux field.

17. The system of claim 3, wherein an RF transponder and an RF reader in synchronicity are together configured with respect to ascribed RF transducer system alignment parameters, to provide for detecting and processing a predetermined modulated second electromagnetic flux field signal provided by an RF tag, whereby:

presence of an RF tag, even if non-ideally aligned, may be established;

distance to an RF tag may be resolved and determined;

additional alignment parameters associated with proximal placements of an RF reader to an RF tag, and inherent geometric configurations which occur between them, including perpendicularity, centering, and obliqueness, may be resolved and determined;

predetermined digital data stored in an RF tag may be recovered, reconstructed, and/or stored, and, responded to;

assorted predetermined RF transponder functions and responses may occur, and be indicated; and predetermined RF reader components or devices may reflect assorted RF transponder functions and/or responses.

18. The system of claim 17, wherein an RF transponder may predeterminedly perform assorted functions with respect to ascribed RF transducer system alignment parameters, variably comprised of:

means for providing assorted utilities and system operations, automatically and/or in a selectable fashion by a user, depending on application, configuration, need, or desire;

means for indicating at least one operating status of the system;

means for monitoring at least one device or component associated with the system, and predeterminedly indicating the status thereof;

means for monitoring at least one signal associated with the system, and predeterminedly indicating the status thereof;

means for monitoring at least one operating attribute associated with the system, and predeterminedly indicating the status thereof;

means for monitoring at least one environmental condition associated with the system, and predeterminedly indicating the status thereof;

means for providing control of an intelligent display device, wherein a user might note and be able to select at least one system function, and obtain feedback regarding system operations;

means for providing assorted responses to user commands and/or user input;

means for providing for a plurality of reader drive waveforms;

means for providing for a plurality of reader drive frequencies;

means for providing for the detection and acquisition of signals emitted from an RF tag;

means for providing for predetermined filtering of signals acquired from an RF tag;

means for providing for reconstruction of digital data embedded in acquired RF tag signals;

means for providing assorted responses to acquired and/or reconstructed RF tag data signals; and means for providing for the programming of memory associated with an RF tag.

19. The system of claim 17, wherein an RF reader is further configured with respect to ascribed RF transducer system alignment parameters, to reflect and provide indication of at least one RF transponder function and/or at least one RF transponder response to an acquired RF tag signal, by means of components variably comprised of:

at least one predefined light emitting diode device; and a predefined audio device.

20. The system of claim 17, wherein an RF transponder is further configured with respect to ascribed RF transducer system alignment parameters, with an electronics assembly, variably comprised of:

a power supply control and conditioning circuit;

electronic devices, configured to select and effect at least one internal reader drive waveform and frequency with which to apply to at least one capacitor, to provide for resonance of the capacitor and a thereto attached coil of an RF reader, thereby to ultimately create emissions of a first predetermined electromagnetic flux field;

passive and analog circuit devices, including amplifiers, configured to detect, filter, and enhance the modulated second predetermined electromagnetic flux field signal provided by an excited RF tag, wherein indications of an RF tag presence, distance, and other alignment criterion might ultimately be provided for, and wherein at least one reconstructed RF tag data signal might ultimately be obtained;

digital circuit devices, configured to control and route assorted signals to, from, and within the electronics assembly;

a microcontroller device, configured to control assorted analog and digital circuitries, monitor a plurality of system parameters, control the routing of assorted signals to, from, and within the electronics assembly, and, process and predeterminedly respond to user input and at least one reconstructed RF tag data signal;

a user interface apparatus;

at least one external device or apparatus interface circuit; and at least one connection means providing for the attachment of an RF reader apparatus.

21. The system of claim 20, wherein and with respect to ascribed RF transducer system alignment parameters, a microcontroller device minimally comprises:

a first (RAM/EE/etc) memory array, to store, retrieve, and manipulate information associated with user input, system and program variables, and other data, including at least one reconstructed data signal obtained from an excited RF tag;

a second (ROM/EE/FLASH/etc) memory array, to retain, recall, and execute at least one software program, and store system and program constants or other data; and I/O (input/output) control pins or connections, to monitor, direct, and manipulate circuitries associated with, but external to, the microcontroller device.

22. The system of claim 20, wherein a user interface apparatus of an RF transponder may be configured with respect to ascribed RF transducer system alignment parameters, to be variably comprised of:

at least two predefined pressure, capacitive, resistive, optical, or mechanical switches, singularly or in combination, providing for system control and user input, and creating in essence, a keyboard;

at least one predefined light emitting diode device;

a predefined alphanumeric and/or graphic display device; and a predefined audio device.

23. The system of claim 20, wherein external device interface circuit of an RF transponder may be configured with respect to ascribed RF transducer system alignment parameters, to be variably comprised of:

a first data transceiving circuit attached to at least one I/O control pin of a microcontroller apparatus, wherein first data transceiving circuit is additionally attached to a predefined printer port connector device, providing thereby, for attachment of an external printer device or apparatus to an RF transponder;

a second data transceiving circuit attached to at least one I/O control pin of a microcontroller apparatus, wherein second data transceiving circuit is additionally attached to a predefined communications port connector device, providing thereby, for attachment of an external computer or other communications-enabled device or apparatus to an RF transponder; and an external device or apparatus control circuit attached to at least one I/O control pin of a microcontroller apparatus, wherein external device or apparatus control circuit is additionally attached to a predefined connector device, providing thereby, for attachment of an x-ray emitting machine or apparatus to an RF transponder, and additionally providing for control and/or operation of an x-ray emitting machine or apparatus, in part or whole.

24. A method for aligning a RF tag to a RF reader with respect to ascribed RF transducer system alignment parameters, variably comprising:
selecting and enabling an RF drive waveform and frequency, by means of control signals provided for by an RF transponder;
applying a predefined drive waveform and RF frequency to a capacitor attached to an RF reader, providing for collective resonance of the capacitor and at least one coil device associated with an RF reader, by means of control signals provided for by an RF transponder;
emitting from an RF reader, a first electromagnetic flux field;
manipulating an RF reader proximally to an RF tag, or vise versa;
receiving from an RF reader, a first electromagnetic flux field by an RF tag, providing for resonance of circuitries associated with the RF tag;
emitting from an RF tag, a modulated second electromagnetic flux field;
receiving from an RF tag, a modulated second electromagnetic flux field by an RF reader;
detecting a received modulated second electromagnetic flux field, by an RF transponder;
observing the presence of an RF tag, by means of indication provided for by an RF transponder;
conditioning and processing a received modulated second electromagnetic flux field by an RF transponder, attaining at least one reconstructed RF tag data signal during the positioning of an RF reader to an RF tag;
observing the distance of an RF tag from an RF reader, by means of indication provided for by an RF transponder;
observing various geometric or other positional alignment conditions between an RF tag and an RF reader, by means of indication provided for by an RF transponder;
maneuvering, if need be, an RF reader proximally to an RF tag, or vise versa, to attain enhanced positioning of the RF reader and RF tag to one another; and
observing at least one predeterminedly ascribed critical alignment condition between an RF tag and an RF reader, by means of indication provided for by an RF transponder.

25. The method of claim 24, further comprising:
embedding digitally formatted data within a second electromagnetic flux field emitted by an RF tag, thereby modulating the emitted second electromagnetic flux field;
receiving an emitted second electromagnetic flux field embedded with digital data, by an RF reader;
detecting an emitted second electromagnetic flux field received by an RF reader, by an RF transponder;
recovering digital data embedded within an emitted second electromagnetic flux field received by an RF reader, by an RF transponder;
analyzing at least one portion of the recovered digital data, by an RF transponder;
storing at least one portion of said recovered digital data, by an RF transponder;
responding to at least one portion of the recovered digital data in at least one predetermined manner, by an RF transponder;
displaying at least one portion of the recovered digital data, by an RF transponder; and
communicating at least one portion of the recovered digital data to external devices or apparatus.

26. The method of claim 24, further comprising:
placing an RF reader upon or about the active portion of an x-ray emitting machine or apparatus.

27. The method of claim 24, further comprising:
embedding or attaching an RF tag to an x-ray sensitive film or apparatus, and/or, embedding or attaching an RF tag to an x-ray film holder or digital imaging apparatus, creating in essence an imaging alignment appliance assembly;
predeterminedly placing an imaging alignment appliance assembly in a patient's mouth if the intended imaging procedure is dental oriented, or, about a patient's body if the intended imaging procedure is other than dental oriented;
maneuvering the active portion of an x-ray emitting apparatus about a patient's mouth or body until a predefined or desired RF tag to RF reader alignment is achieved, or, positioning a patient's mouth or body about the active portion of an x-ray emitting apparatus until a predefined or desired RF tag to RF reader alignment is achieved; and
with predefined RF tag to RF reader alignment achieved, activating the x-ray emitting apparatus to obtain a radiograph.

28. A method providing for configuring RF transducer system alignment parameters in an RF transponder system, whether by means of firmware, user input devices, control signals, or other means, or combination thereof, provided about, to, or within a preconfigured RF transponder, and, with respect to relative, positional or geometric relationships which can exist between proximally placed RF tags and RF readers, and, as may be intended to be sensed, distinguished, evaluated, and predeterminedly responded to by a preconfigured RF transponder, variably comprising:
selecting at least one value relative to an ascribed distance between an RF tag and an RF reader, providing therein for selectively-adjustable preset or user-defined system-reference set-points relative to distance, therewith providing for predefined enabling or disabling of one or more RF transponder system operations when a system-sensed RF tag to RF reader distance is determined to be less than, greater than, or equal to an ascribed preset or user-defined distance value;
selecting at least one set of window limit values relative to an ascribed range of operation, providing therein for selectively-adjustable apertures of specific range, each of which is composed of a first preset or user-defined near-field limit value in addition to a second preset or user-defined far-field limit value, also providing for system-reference window-limit set-points, therewith providing for predefined enabling or disabling of one or more RF transponder system operations when a system-sensed RF tag to RF reader distance is determined to be within, or outside of, a preset or user-defined range of operation and set of window limit values;
selecting at least one first geometric or other alignment parametric value as concerns ascribed placement of an RF tag to two or more RF reader coils, providing for conditions when system-sensed signal differences obtained from, and between the individual coil outputs reflect a predetermined offset or displacement of an RF tag in three dimensional space relative to each coil, therewith providing for myriad calculable positional arrangements, and the predefined enabling or disabling of one or more RF transponder system operations when a system-sensed RF tag to RF reader arrangement is determined to be less than, greater than, or equal to a given preset or user-defined geometric alignment value, further providing for RF transducer system responsiveness to a plurality of inherent geometric configuration potentialities, including those of obliqueness, perpendicularity, and parallelism;

selecting a subsequent geometric or other alignment parametric value as additionally concerns ascribed placement of an RF tag to two or more RF reader coils, providing for conditions when system-sensed signal values obtained from, and between the individual coil outputs reflect a null offset or zero displacement of an RF tag in three dimensional space relative to each coil, therewith providing system capability to denote a uniformly equal positional arrangement, thus providing for predefined enabling or disabling of one or more RF transponder system operations when a system-sensed RF tag to RF reader arrangement is determined to be equilateral, further providing for RF transducer system responsiveness to the inherent geometric configuration potentiality of centering; and selecting additional parameters relative to alignment as concerns allowable deviation from a given preset, user setting, limit or set-point, whereby a parametric alignment signal to be evaluated may also be evaluated over an ascribed deviational tolerance range, rather than evaluated to an absolute.

29. The method of claim 28, further comprising:

providing for at least one indication by an RF transducer system, by print-out, audio or visual means, or intelligent display apparatus, or a combination thereof, of ascribed parametric alignment conditions;

providing for indication by an RF transducer system, of selected preset or user defined settings, limits, setpoints and tolerances associated with each ascribed alignment parameter, insuring an RF transducer system might provide for indicating the present configuration of one or more alignment parameters;

providing for indication by an RF transducer system, of the system-sensed and processed parametric alignment values or conditions determined to exist, moment by moment, for each selected and ascribed alignment parameter;

providing for indication by an RF transducer system, of when the system-sensed and processed parametric values or conditions determined to exist for each ascribed alignment parameter have been neared, achieved, or exceeded;

providing for indication by an RF transducer system, of when an ascribed and system-sensed critical-alignment condition between an RF tag and RF reader has been attained, or not; and additionally providing for means to set, enable and disable one or more predefined system alarms, providing for indication of when an ascribed and system-sensed alignment parameter signal is equal to, less than, or greater than, or in predetermined combination thereof, a given preset, user setting, limit, set-point or tolerance for that alignment parameter.

30. A method providing a plurality of attachment configurations of a RF reader to a RF transponder with respect to ascribed RF transducer system alignment parameters, variably comprised of:

a multi-wire interface cable apparatus applied between an RF reader and an RF transponder, wherein both the RF reader and RF transponder provide for a predetermined interface cable receiving means, and wherein an RF reader is remotely positioned from an RF transponder by a predetermined distance, additionally providing for interchangeability in that alternate RF readers may be attached to an RF transponder, further providing for a fixed or variable RF alignment assembly, collectively comprised of an interface cable, an RF reader, and an RF transponder;

a connector device attached about an RF reader to mate with a connector device attached about an RF transponder, providing for temporary or permanent fixation of an RF reader directly to an RF transponder without the use of a cable, additionally providing for interchangeability in that alternate RF readers may be attached to an RF transponder, further providing for a fixed or variable RF alignment assembly, collectively comprised of an RF reader and an RF transponder; and electrical conductor receiving means about an RF transponder to receive electrical conductors about an RF reader, wherein an RF reader is desired to be permanently attached to an RF transponder, providing for an integrally affixed RF alignment assembly, collectively comprised of an RF reader and an RF transponder.

31. The method of claim 30, further configured with respect to ascribed RF transducer system alignment parameters, for a plurality of installation conventions of an RF reader and an RF transponder as a collective RF alignment assembly on or about imaging, medical, or other equipment or apparatus, comprising:

providing for temporary fixation of said collective assembly;

providing for permanent fixation of said collective assembly;

providing for permanent or temporary fixation of an RF reader; and providing for permanent or temporary fixation of an RF transponder.

32. The method of claim 30, further configured with respect ascribed RF transducer system alignment parameters, for a plurality of usage conventions of an RF reader and an RF transponder as a collective RF alignment assembly, comprising:

providing for fixed-in-place utility, wherein an RF reader and an RF transponder are predeterminedly positioned and affixed;

providing for portable utility, wherein the attachment(s) of an RF reader and an RF transponder permit transportation of the collective assembly if desired;

providing for hand-held utility, wherein an RF reader and an RF transponder are predeterminedly packaged together forming a single article, and wherein a handle apparatus integral to the single article permits positioning of the single article freely about in 3 dimensional space; and providing for flexible utility, wherein an RF reader may be positioned or repositioned about, and independent to, the position and location of an RF transponder.

33. A method with respect to ascribed RF transducer system alignment parameters, providing for a plurality of operating conventions between an RF tag, and an RF transponder coupled to an RF reader, and further providing options with regard to specialized alignment applications in a medical or other environment, comprising:
provide for discretionary responses to an RF transponder, by an RF tag; and
providing for discretionary inquiries of, or discretionary communications to, an RF tag, or a variety of pre-configured RF tags, by an RF transponder.

34. The method of claim 33, further comprising:
responding when deemed appropriate to a received first electromagnetic flux field provided by an RF reader, by an RF tag, by means of applying predefined digital data to a signal dampening circuit attached about a selected and integral LC tank circuit, therewith to predeterminedly modulate the LC tank circuit and a second predetermined electromagnetic flux field of the RF tag;
examination of at least one magnitude of a received first electromagnetic flux field provided by an RF reader, by an RF tag;
election of whether or not to respond to an RF transponder, predicated on a given magnitude, or magnitudes, of a received first electromagnetic flux field provided by an RF reader, by an RF tag; and
election of what predefined data, if any, to respond with to an RF transponder, by an RF tag, predicated on at least one predefined magnitude of a received first electromagnetic flux field provided by an RF reader.

35. The method of claim 33, further comprising:
responding when deemed appropriate to a received first electromagnetic flux field provided by an RF reader, by a predefined RF tag, by means of applying predefined digital data to a signal dampening circuit attached about a selected and integral LC tank circuit, therewith to predeterminedly modulate the LC tank circuit and a second predetermined electromagnetic flux field of the RF tag;
examination of at least one frequency of a received first electromagnetic flux field provided by an RF reader, by an RF tag;
election of whether or not to respond to an RF transponder, predicated on a given frequency, or frequencies, of a received first electromagnetic flux field provided by an RF reader, by an RF tag; and
election of what predefined data, if any, to respond with to an RF transponder, by an RF tag, predicated on at least one predefined frequency of a received first electromagnetic flux field provided by an RF reader.

36. The method of claim 33, further comprising:
at least one security attribute of an RF tag, providing for predefined multi-level access to RF tag data by an RF transponder; and
at least one security attribute of an RF tag providing for predefined multi-level responses to an RF transponder, by an RF tag.

37. The method of claim 33, further comprising:
generating a first electromagnetic flux field of a predefined magnitude, by an RF reader attached to, and in synchronicity with, an RF transponder; and
generating a first electromagnetic flux field of at least one predefined frequency, by an RF reader attached to, and in synchronicity with, an RF transponder.

38. The method of claim 33, providing for discretionary inquiries of, or discretionary communications to, an RF tag, or a variety of pre-configured RF tags, by an RF transponder, further comprising:
emissions of a first electromagnetic flux field of a predefined magnitude, or magnitudes, by an RF reader, wherein an RF transponder has the capacity to denote an assortment of variously configured RF tags with respect to at least one parameter of alignment, has the capacity to predeterminedly interrogate an RF tag, has the capacity to provide predetermined recognition to an RF tag, has the capacity to communicate at least one predetermined command or instruction to an RF tag, and has the capacity to access at least one level of data stored in an RF tag; and
emissions of a first electromagnetic flux field of a predefined frequency, or frequencies, by an RF reader, wherein an RF transponder has the capacity to denote an assortment of variously configured RF tags with respect to at least one parameter of alignment, has the capacity to predeterminedly interrogate an RF tag, has the capacity to provide predetermined recognition to an RF tag, has the capacity to communicate at least one predetermined command or instruction to an RF tag, and has the capacity to access at least one level of data stored in an RF tag.

39. The method of claim 33, further comprising:
at least one security attribute providing for pre defined access to a plurality of RF tags, by an RF transponder;
at least one security attribute providing for predefined access to predefined data stored within a plurality of RF tags, by an RF transponder;
at least one communicative attribute of an RF transponder, providing for predefined responses from a plurality of RF tags;
at least one communicative attribute providing for predefined control of a plurality of RF tags, by an RF transponder;
at least one communicative attribute providing for predefined access to a plurality of RF tags, by an RF transponder; and
at least one communicative attribute providing for predefined access to a plurality of predefined data stored within a plurality of RF tags, by an RF transponder.

40. The method of claim 33, further comprising:
means providing for variable frequency hopping by an RF transponder, wherein and predicated on environmental EMI (electromagnetic interference) conditions, one frequency might be automatically or manually selected over another frequency to best achieve RF correspondence with, or an RF link to, an RF tag.

41. A method with respect to ascribed RF transducer system alignment parameters, providing for a plurality of RF transponder operating conventions, and further providing options with regard to specialized alignment applications in a medical or other environment, comprising:
utilizing multiple coil devices of same or dissimilar size about an RF reader, thereby;
providing for selection of one or more first electromagnetic flux field magnitudes;
providing for selection of one or more first electromagnetic flux field strengths;
providing for selection of frequency of one or more first electromagnetic flux fields; and
providing for selective receiving of one or more second electromagnetic flux fields.

42. A system for obtaining dental and other medical x-rays with respect to ascribed RF transducer system alignment parameters, comprising:
an x-ray emitting machine or apparatus;
a film or apparatus sensitive to x-ray emissions;
an RF reader mechanically attached to, or embedded with, an x-ray emitting machine or apparatus, wherewith said RF reader is additionally and electrically attached to an RF transponder, and wherein a first electromagnetic flux field is emitted by an RF reader, and wherein an RF reader is responsive to emissions of a second electromagnetic flux field;

an RF tag, intimately associated with an x-ray sensitive film or apparatus, and/or, an x-ray film holder or digital imaging apparatus, configured to emit a modulated second electromagnetic flux field when predeterminedly excited by a first electromagnetic flux field emitted from an RF reader; and an RF transponder, configured to control and be responsive to an RF reader, and further configured to detect and process modulated second electromagnetic flux fields emitted from an excited RF tag as received by an RF reader, and while processing received RF tag emissions, denote geometric and other alignment parameters reflective of the proximal placement of an RF tag to an RF reader.

43. The system of claim 42, further comprising:

means for preventing the operation of an x-ray machine or apparatus when predefined RF tag to RF reader alignment conditions are not realized; and means for allowing an x-ray machine or apparatus to operate when predefined RF tag to RF reader alignment conditions are realized.

44. The system of claim 42, further comprising:

means for programming patient and other information into an RF tag;

means for retrieving patient and other information from an RF tag;

means for storing patient and other information from an RF tag;

means for inputting user, patient, and other information into an RF transponder;

means for manipulating user, patient, and other information in an RF transponder;

means for communicating received data from an RF tag, or other data, to or with predefined equipment, such as an external printer or personal computer, or other device;

means for providing for operation of the RF transducer alignment system, in part or whole, by means of communication with or from predefined equipment or apparatus, such as an external personal computer, or other device or apparatus;

means for providing for at least one integral or remotedly attached RF reader, and;

means for providing for those governing signals and/or circuitries and/or devices which may assist or permit control of external apparatus, such as: an x-ray emitting/imaging machine or device, an MRI (magnetic resonance imaging) machine or device, or a medical-treatment radiation machine or device, in part or whole.

45. The system of claim 42, yet further comprising:

means for controlling the gain functions of one or more amplifier circuits;

means for controlling the filter functions of one or more amplifier circuits;

means for providing for selection of one or more amplifier circuits;

means for detecting and indicating electrical continuity between an RF reader and an RF transponder, providing for notice of acceptable installation of an RF reader, or lack thereof;

means for detecting and indicating operation, or the lack thereof, of an RF reader;

means for detecting and indicating one or more resonant voltages of an RF reader coil device;

means for detecting and indicating one or more resonant frequencies of an RF reader;

means for utilizing variously sized RF readers, singularly, or in plurality, by an RF transponder;

means for utilizing RF readers constructed of same or of differing coil inductances, singularly, or in plurality, by an RF transponder;

means for utilizing a plurality of RF readers, each constructed with one or more coil devices, with each coil device operating at the same, or dissimilar, frequencies, by an RF transponder;

means for indicating at least one selected and/or active RF reader;

means for selecting and controlling the reader drive frequency of an RF transponder, thereby, defining the applied operating frequency of an RF reader, or coil device thereof, and thus controlling the operation of an RF reader;

means for indicating one or more selected reader drive frequencies of an RF transponder;

means for selecting and controlling the reader drive waveform of an RF transponder applied to a capacitor attached to, and operated in resonance with, a coil of an RF reader, thereby providing a capacity to modify and tune or detune a given waveform and apply a given waveform to the capacitor;

means for indicating one or more selected reader drive waveforms of an RF transponder;

means for detecting and processing the same or dissimilar RF emissions from a plurality of RF tags;

means for utilizing a plurality of RF transponders;

means for utilizing a multiplicity of RF tags and RF readers, wherein each RF tag is responsive only to a given RF reader, and vise versa, or, wherein any RF tag is responsive to any given RF reader, and vise versa, or, wherein a given RF tag is responsive to multiple RF readers, and vise versa, or, wherein a selective combination of the foregoing is employed; and means for utilizing at least one RF transponder and a predefined collection of RF tags and RF readers, in at least one geometric, planar oriented, or other physically spatial configuration, whereby a plurality of indications pertaining to alignment parameters, including distance, position, attitude, inclination, or orientation can be realized, and whereby multi-axis, multi-planar, or a mixture of arrangements and applications can be provided for, and whereby an enhanced operational feature and a yet additional alignment parameter recognized as triangulation can be provided for.

* * * * *